(12) United States Patent
Liu et al.

(10) Patent No.: US 8,271,206 B2
(45) Date of Patent: Sep. 18, 2012

(54) DNA SEQUENCE ASSEMBLY METHODS OF SHORT READS

(75) Inventors: Changsheng Jonathan Liu, State College, PA (US); Yiqiong Wu, Fayetteville, AR (US); Kevin Jay LeVan, State College, PA (US)

(73) Assignee: SoftGenetics LLC, State College, PA (US)

( * ) Notice: Subject to any disclaimer, the term of this patent is extended or adjusted under 35 U.S.C. 154(b) by 389 days.

(21) Appl. No.: 12/427,409

(22) Filed: Apr. 21, 2009

(65) Prior Publication Data

US 2009/0318310 A1    Dec. 24, 2009

Related U.S. Application Data

(60) Provisional application No. 61/046,632, filed on Apr. 21, 2008.

(51) Int. Cl.
*G06F 19/00* (2011.01)
*G06F 15/00* (2006.01)

(52) U.S. Cl. ............................................. 702/20; 700/1

(58) Field of Classification Search ........................ None
See application file for complete search history.

(56) References Cited

U.S. PATENT DOCUMENTS

2008/0189049 A1*  8/2008  Zhang .............................. 702/20

OTHER PUBLICATIONS

Warren et al., Bioinformatics, Vo. 23, No. 4, pp. 500-501. 2007.*
Wikipedia for Hash Table, printed from http://en.wikipedia.org/wiki/Hash_table on Aug. 15, 2011.*
Zerbino, "Velver: Algorithms for de novo short read assembly using de Bruijn graphs", Genome Research, (Mar. 18, 2008) vol. 18, pp. 821-829.
Li et al., "Mapping short DNA sequencing reads and calling variants using mapping quality scores", Genome Research, (Aug. 19, 2008), vol. 18, pp. 1851-1858.

* cited by examiner

*Primary Examiner* — John S Brusca
(74) *Attorney, Agent, or Firm* — The Webb Law Firm

(57) ABSTRACT

Certain embodiments of the invention provide systems and methods for the automated assembly of DNA sequence data into contiguous DNA segments using a computer a system. DNA sequence data is entered into the system. The system indexes and groups a plurality of DNA fragment reads utilizing an anchor sequence and consolidates the fragments into larger sequences by merging the fragment reads within a group.

19 Claims, 18 Drawing Sheets

| Index | Reference Position | Reference Nucleotide | Coverage | A (%) | C (%) | G (%) | T (%) | Ins (%) | Del (%) | SNP db_xref | Genotype | Mutation Call | AminoAcid: Change |
|---|---|---|---|---|---|---|---|---|---|---|---|---|---|
| 57 | 4848 | T | 18 | 0.00 | 0.00 | 22.22 | 77.78 | 0.00 | 0.00 | | GT | T>GT | |
| 58 | 4849 | C | 18 | 44.44 | 55.56 | 0.00 | 0.00 | 0.00 | 0.00 | | AC | C>AC | |
| 59 | 4936 | G | 42 | 0.00 | 0.00 | 76.19 | 21.43 | 0.00 | 0.00 | | GT | G>GT | |
| 60 | 6396 | T | 459 | 0.87 | 94.55 | 0.00 | 4.58 | 0.00 | 0.00 | dbSNP:1 | CC | T>C | |
| 61 | 9626 | C | 534 | 2.25 | 8.61 | 2.25 | 86.89 | 0.00 | 0.00 | dbSNP:2 | TT | C>T | |
| 62 | 7008 | T | 192 | 0.00 | 0.00 | 0.00 | 77.60 | 0.00 | 22.40 | | delTTT | delTTT | |
| 63 | 7009 | T | 212 | 0.00 | 0.00 | 0.00 | 79.25 | 0.00 | 20.75 | dbSNP:5 | - | - | |
| 64 | 7010 | T | 224 | 0.00 | 0.00 | 0.00 | 79.91 | 0.00 | 20.00 | | - | - | |
| 65 | 7118 | A | 631 | 3.65 | 0.00 | 96.35 | 0.00 | 0.00 | 0.00 | dbSNP:1 | GG | A>G | |
| 66 | 7753 | G | 201 | 0.00 | 73.13 | 26.87 | 0.00 | 0.00 | 0.00 | dbSNP:1 | CG | G>CG | 72P>RP |
| 67 | 8082 | G | 106 | 0.00 | 64.15 | 35.85 | 0.00 | 0.00 | 0.00 | dbSNP:1 | CG | G>CG | |
| 68 | 8510 | G | 9 | 0.00 | 0.00 | 55.56 | 44.44 | 0.00 | 0.00 | | GT | G>GT | |
| 69 | 8517 | A | 9 | 66.67 | 33.33 | 0.00 | 0.00 | 0.00 | 0.00 | | AC | A>AC | |
| 70 | 8685 | A | 10 | 0.00 | 0.00 | 100.00 | 0.00 | 0.00 | 0.00 | | GG | A>G | |

FIG. 15

DNA SEQUENCE ASSEMBLY METHODS OF SHORT READS

This application is based on U.S. Provisional Patent Application No. 61/046,632, filed Apr. 21, 2008, on which priority of this patent application is based and which is hereby incorporated by reference in its entirety.

The Sequence Listing associated with this application is filed in electronic format via EFS-Web and is hereby incorporated by reference into the specification in its entirety. The name of the text file containing the Sequence Listing is 5765-090671_ST25.txt. The size of the text file is 33,930 bytes, and the text file was created on Jan. 13, 2012.

BACKGROUND OF THE INVENTION

1. Field of the Invention

The present invention relates to the field of bioinformatics, specifically to the field of the automated alignment and merging short DNA fragments, and the assembly of these fragments into larger DNA molecules.

2. Description of Related Art

The field of bioinformatics involves the practice of sequence assembly, which refers to the aligning and merging of smaller fragments of a much larger DNA sequence in order to reconstruct that original large sequence. Current sequence technology does not allow the sequencing of very large DNA fragments. Instead, smaller pieces, generally between 20 and 1000 bases, are sequenced and then merged.

The problem of sequence assembly can be compared to passing multiple copies of a book through a shredder and then attempting to piece a single copy of the book back together from only shredded pieces. The resulting book may have many repeated paragraphs while some shreds may be modified to have typos. Excerpts from another book may be added in and some shreds may be completely unrecognizable.

Current sequencing techniques rely on breaking large DNA fragments into small fragments which are then individually sequenced. This procedure is performed in a redundant or overlapping procedure in a way that maximizes the likelihood that all the portions of the larger DNA fragments are sequenced one or more times by the sequencing of the overlapping small fragments. This process results in a logic, or computational problem in that the sequences of the small fragments must be assembled or aligned into larger pieces, which larger pieces are then assembled into still larger pieces in order to create the entire DNA sequence of the large fragment sought to be sequenced.

DNA is a biochemical polymer made up of monomers referred to as "bases" which are conventionally represented by one of four letters, A, T, C, or G. As used herein, the small piece of DNA which is subjected to actual biochemical analysis to determine its base sequence is referred to as a "fragment," and the data representing the DNA sequence generated from each fragment is referred to as a "fragment read". Again, in the overall sequencing process, fragment reads are created which are redundant or overlapping to cover most or all sections of the larger DNA piece from which the overlapping was created. The fragment reads must be aligned into one or more contiguous larger segments, such a larger segment being referred to here as a "contig". The overall layout of fragments into contigs is used to determine the sequence of large fragments of DNA. This process is referred to here as "fragment assembly".

Because DNA is a polymer, it is common to refer to DNA pieces using the nomenclature of polymers. Hence, the terminology "mer" is used to refer to a sequence of bases in a fragment read. In the conventional terminology used, "mer" refers to a sequence of any length and, when prefixed with the number, is used to refer to a sequence of defined length. Thus a 20-mer is a portion of DNA 20 bases in length.

Technological development of sequencing continues to improve. The Solexa™ technology is available and heavily used to generate roundabout 100 million reads per day on a single sequencing machine. Compare this to the 35 million reads of the human genome project which needed several years to be produced on hundreds of sequencing machines. The downside is that these reads have a length of only 36 bases. This makes sequence alignment an even more daunting task.

SUMMARY OF THE INVENTION

In one aspect, the current invention relates to a method for automated assembly of DNA sequence data that includes DNA fragment reads into contiguous DNA segments using a computer system with processing and information storage capabilities, the method including the steps of: entering into the computer storage information representing the DNA sequence data from a plurality of DNA fragment reads; indexing the fragment reads using an anchor sequence, the anchor sequence an occurrence of a mer of length n, whereby a fragment read is indexed by at least one anchor sequence; grouping fragment reads according to said anchor sequence; and consolidating the grouped fragment reads into larger sequences by merging fragment reads within a group of fragment reads. In another aspect, this method further includes the steps of: grouping fragment reads grouped according to an anchor sequence into further subgroups according to a similar shoulder sequence; and matching sequence reads within each subgroup thereby creating assemblies of said sequence reads within each respective subgroup. In an additional aspect, the method also includes the step of elongating at least one fragment read by pooling consolidated regions of indexed areas of said fragment read to assemble the fragment reads into contiguous segments of DNA sequence.

In one embodiment of the inventive method, the average read length is increased in the range of 1.4-1.6, and the Indels and/or single nucleotide polymorphisms (SNPs) are preserved. In a further embodiment, the method includes the step of aligning an elongated fragment read to a user defined sequence read to determine SNP and Indels. In another embodiment, the step of grouping fragment reads includes scanning the fragment reads to pick from the mers occurring in each fragment read at least one n-mer, and storing in said computer storage file a fragment read having said n-mer occurrence therein. In a further embodiment, low frequency errors are eliminated, total read counts are reduced and consensus sequence errors are reduced, below 0.5%. In a further embodiment, the anchor sequence is 12 bases.

In one aspect, the present invention pertains to a sequence assembly system for transforming DNA sequence information from DNA fragment reads into contigs of contiguous DNA sequences, including a computer processor, memory, and data storage devices, the memory having programming instructions to operate the computer processor to consolidate a set of fragment reads. In a further aspect, the computer processor outputs to a display a user interface window and the window further displays one or more of a whole genome pane, an aligned sequence pane, and a consensus sequence pane.

In a further embodiment of the inventive system, the programming instructions are operable to: store information representing the DNA sequence data from a plurality of DNA fragment reads; index the fragment reads using an anchor sequence, the anchor sequence an occurrence of a mer of length n, whereby a fragment read is indexed by at least one anchor sequence; group fragment reads according to said anchor sequence; group fragment reads grouped according to an anchor sequence into further groups according to a similar shoulder sequence; and consolidate the grouped fragment reads into larger sequences. In a further aspect, the system further includes the computer processor to output to the display a user preferences window. The preferences including choices to programmatically control the processor of said assembly system with rules, with the rules comprising: Counts Selection Rules; Directional Limitations; Shoulder Selection Rules; and 454 Jumping Rules. In one aspect, the rules include an anchor sequence dynamically adjustable and the 5' ends is given more statistical weight then the 3' ends of the fragment reads.

In an additional embodiment of the invention, the 454 jumping rules further includes slicing a fragment read into multiple sections, where a section includes at least 12-mer fragments and the fragment reads are sliced at the mer positions having greater than 2 homopolymers where the portions of the sequence without large homopolymers are conserved. In a further embodiment, the system also includes programming instructions operable to calculate a known Indel by aligning a consolidated and elongated fragment read with a known reference sequence to determine Indel location. The system may further include programming instructions operable to calculate a known Indel by aligning a consolidated and elongated fragment read with a known reference sequence to determine SNP location.

An additional aspect of the invention comprises a set of computer programming instructions embodied on a computer readable medium for execution on a computer processor having programming instructions thereon for sequence assembly transforming DNA sequence information from DNA fragment reads into contigs of contiguous DNA sequences, comprising instructions operable to consolidate and elongate a set of fragment reads.

In a further embodiment, the present invention pertains to a sequence assembly system for transforming DNA sequence information from DNA fragment reads into contigs of contiguous DNA sequences, that includes: an arrangement for entering into the computer storage information representing the DNA sequence data from a plurality of DNA fragment reads; an arrangement for indexing the fragment reads using an anchor sequence, the anchor sequence an occurrence of a mer of length n, whereby a fragment read is indexed by at least one anchor sequence; an arrangement for grouping fragment reads according to said anchor sequence; and an arrangement for consolidating the grouped fragment reads into larger sequences by merging fragment reads within a group of fragment reads.

BRIEF DESCRIPTION OF THE DRAWINGS

FIG. 15 is an additional exemplary sequence analysis window of the method and system of the invention.

DESCRIPTION OF THE PREFERRED EMBODIMENTS

Figure 1A:
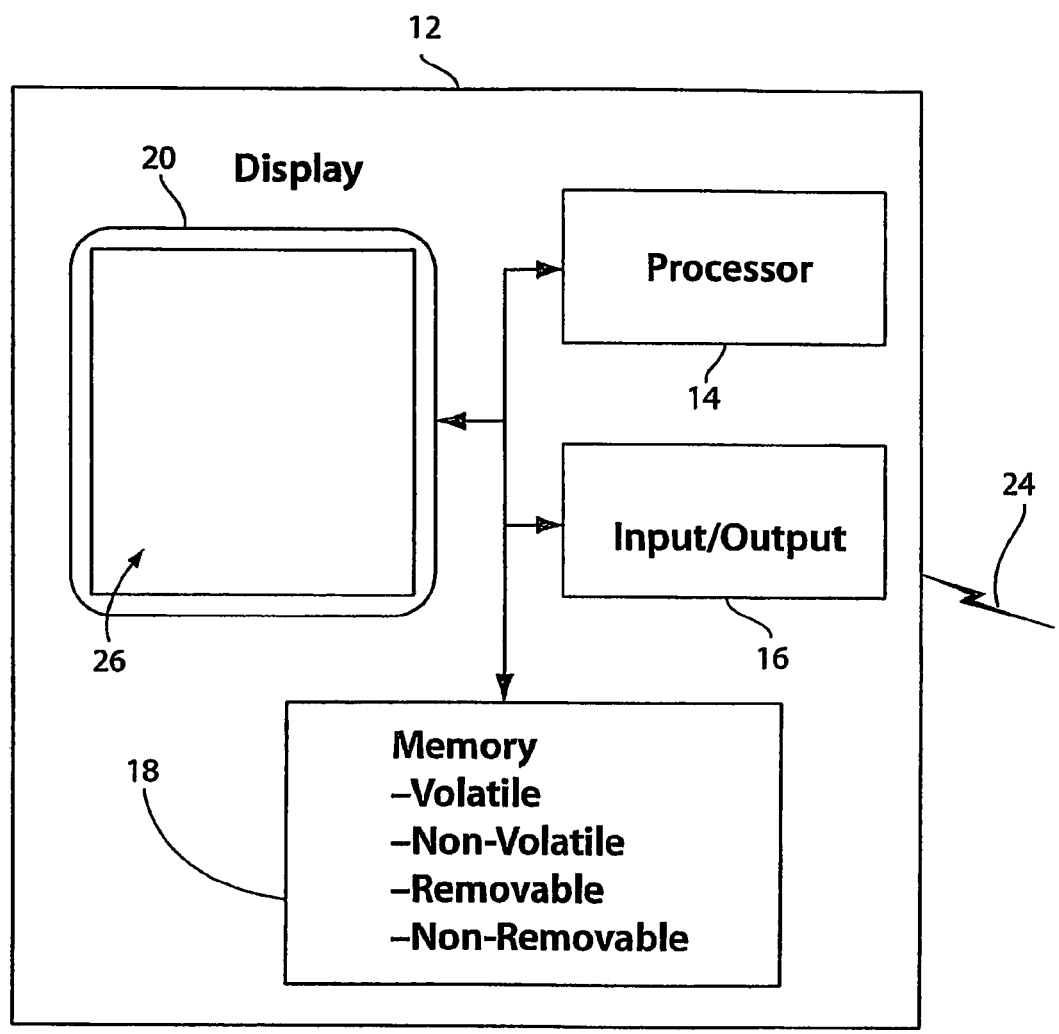
FIG. 1a is a diagram of an exemplary computing device of the invention.

With reference to FIG. 1a, a diagram of an exemplary computing device 12 for implementing a sequence assembly system is shown. In a basic configuration, computing device 12 comprises a processing portion 14, a memory 18, and a display portion 20. Depending upon the exact configuration and type of computing device 12, memory 18 can be volatile (such as RAM), non-volatile (such as ROM, flash memory, etc.), or some combination thereof. Computing device 12 also can include additional features/functionality. For example, computing device 12 also can include additional storage (removable and/or non-removable) including, but not limited to, magnetic or optical disks or tapes. Such additional storage is illustrated in FIG. 1a as part of memory portion 18. Computer storage media includes volatile and non-volatile, removable and non-removable media implemented in any method or technology for storage of information such as computer readable instructions, data structures, program modules, or other data. Memory 18 and any portion thereof, such as removable storage and non-removable storage, can be implemented utilizing computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 12. Any such computer storage media can be part of computing device 12.

Computing device 12 also can include an input/output portion 16 containing communications connection(s) that allow the computing device 12 to communicate with other devices and/or networks via an interface 24. Interface 24 can include a wireless interface, a hard-wired interface, or a combination thereof. Input/output portion 16 also can include and/or utilize communication media. Communication media typically embodies computer readable instructions, data structures, program modules, or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limiting, communication media includes wired media, such as a wired network or direct-wired connection, and wireless media, such as acoustic, RF, infrared, and other wireless media. The term computer readable media as used herein includes both storage media and communication media. Input/output portion 16 also can comprise and/or utilize an input device(s) such as a keyboard, a mouse, a pen, a voice input device, a touch input device, or the like, for example. An output device(s) such as a display, speakers, printer, or the like, for example, also can be included.

Display portion 20 comprises a portion 26 for rendering a DNA sequence assembly window or a portion thereof.

Figure 1B:
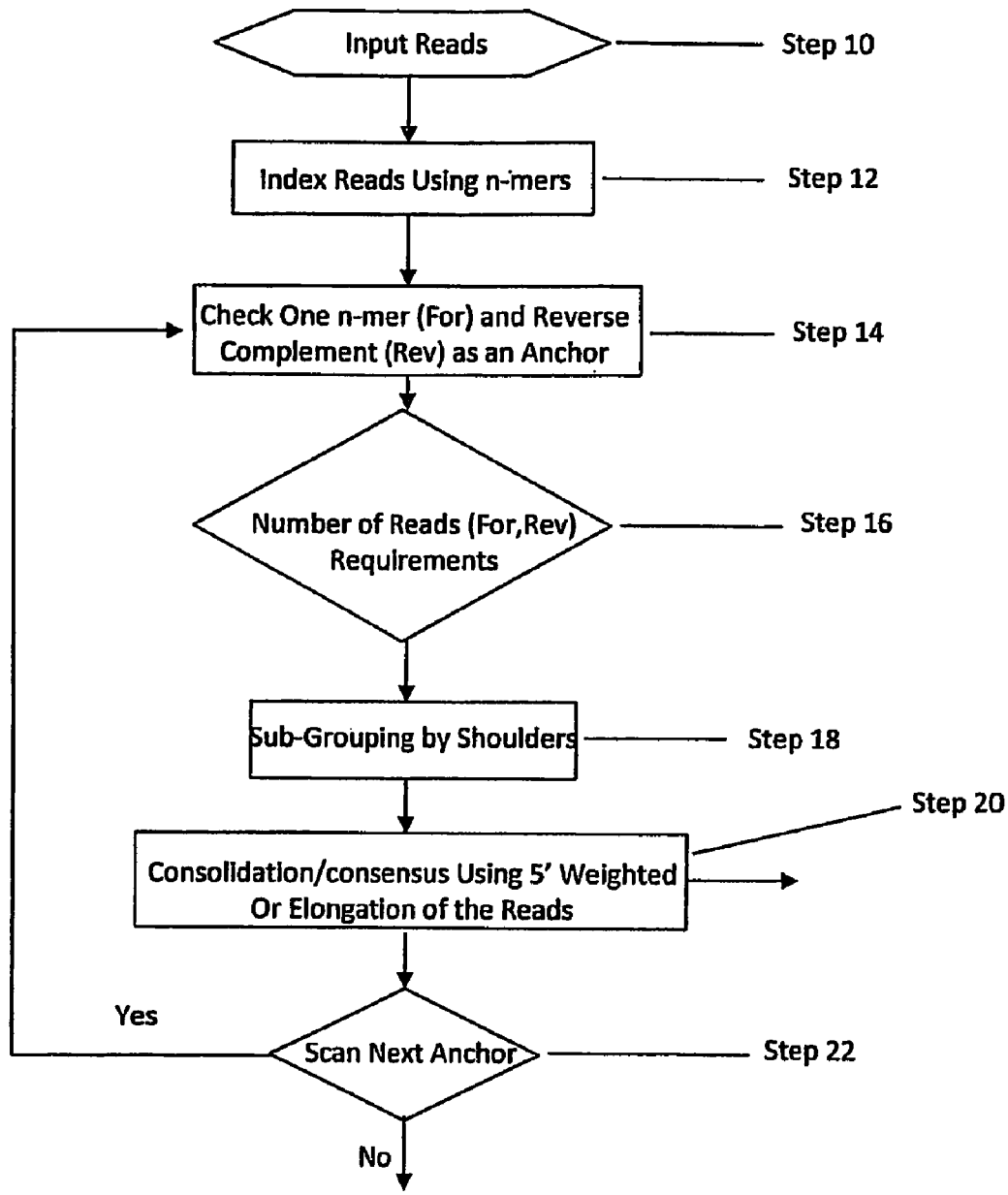
FIG. 1b is a flow chart of the exemplary system of the invention.

The flow chart of FIG. 1b is intended to illustrate, in summary form, the main portions of the computer system for assembling DNA sequence information in accordance with the present invention. The objective is to assemble a series of fragment reads into a contiguous DNA sequence, or contig, using a process in which the processor reads input fragment reads from a file or memory. The method involves scanning a number of input reads into an input file to identify an anchor which is defined by a preset number of mers. At step 10 of FIG. 1b, a computer program operating in accordance with this method first initializes an input file. The DNA sequence information contained in all of the fragment reads is entered into the system either manually or electronically and can be added to a data structure for storage. At step 12, an index is compiled during a scan of the input reads. The scan of step 12 can include each and every fragment read from the input file or can include a smaller subset. Fragment reads are scanned for end n-mers and indexed accordingly. The n-mers are mers of length n, wherein n is a predefined variable. Step 12 results in an index table where n-mers are the index and the number of entries in the table is dependant on the size of the mer and the number of fragment reads. As the number of fragment reads grows, the likelihood that the index will increase grows also since there are more possibilities of indices. Therefore, if n=12, the 12-mer GCTTGTCTAGTCA (SEQ ID NO: 1) could be an anchor in the index. If n=12, the index would be compiled having all mers of the length of twelve bases that occur in the fragment reads. For example, a sequence read of 36 bases is indexed 25 times using 12 mers. The index can also be limited by count and output.

At step 14, the first indexed read from the index file of step 12 is selected. The fragment reads are then checked to determine if the anchor is present. The anchor sequence can be present in the forward direction as well as the complimentary reverse direction. If the anchor is present, the fragment read is grouped. In the preferred embodiment, a group is formed by clustering all fragment reads having the anchor into a file in memory or storage. However, other types of indexing using techniques such as flagging the fragment read in a database can be used. In step 16, the number of reads, both forward and reverse, must meet the requirements stored in the system to trigger its usage as a viable cluster. At step 18, all of the fragment reads that contain the anchor sequence are now clustered together and the clusters can be further limited by subgrouping based on homologous shoulder sequences. Often, many of the reads within the cluster contain homologous shoulders, namely, common mers both upstream and downstream of the anchor sequence. The fragment read clusters can be shouldered by these linking shoulder regions into groups of similarity. At step 20, consolidation takes place. Consolidation includes both condensation and elongation. During the grouping, the original fragment reads were partitioned based on the anchor sequence and then were subdivided again based on the shoulder regions. For example, two different groups can be formed based on the shoulder regions further subdividing the first group. At this point, a consensus sequence can be generated for each group almost doubling the read lengths. Using the condensed sequences, or consensus sequences, an elongation can lengthen the individual fragment reads. At step 20, the 5' end is given more weight than the 3' end statistically because of the higher reliability of the 5' end. At step 20, an output of a consensus sequence, an elongated fragment read, and/or an error corrected fragment read occurs. At step 22, the processor gathers the next anchor sequence and repeats the process back to step 14 as long as the end of the index table has not been reached.

Figure 2:
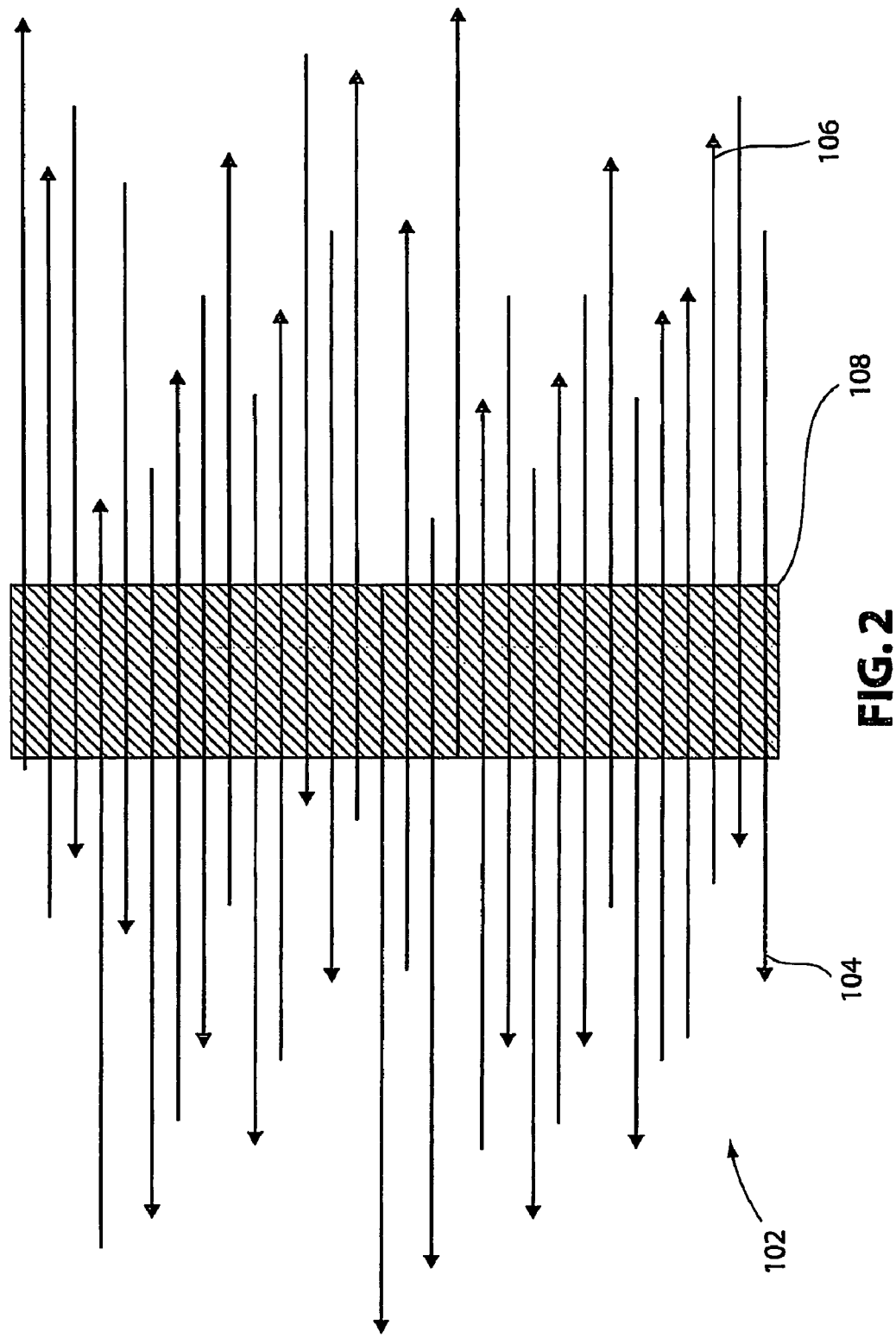
FIG. 2 is an exemplary embodiment of the method of the invention.
Figure 3:
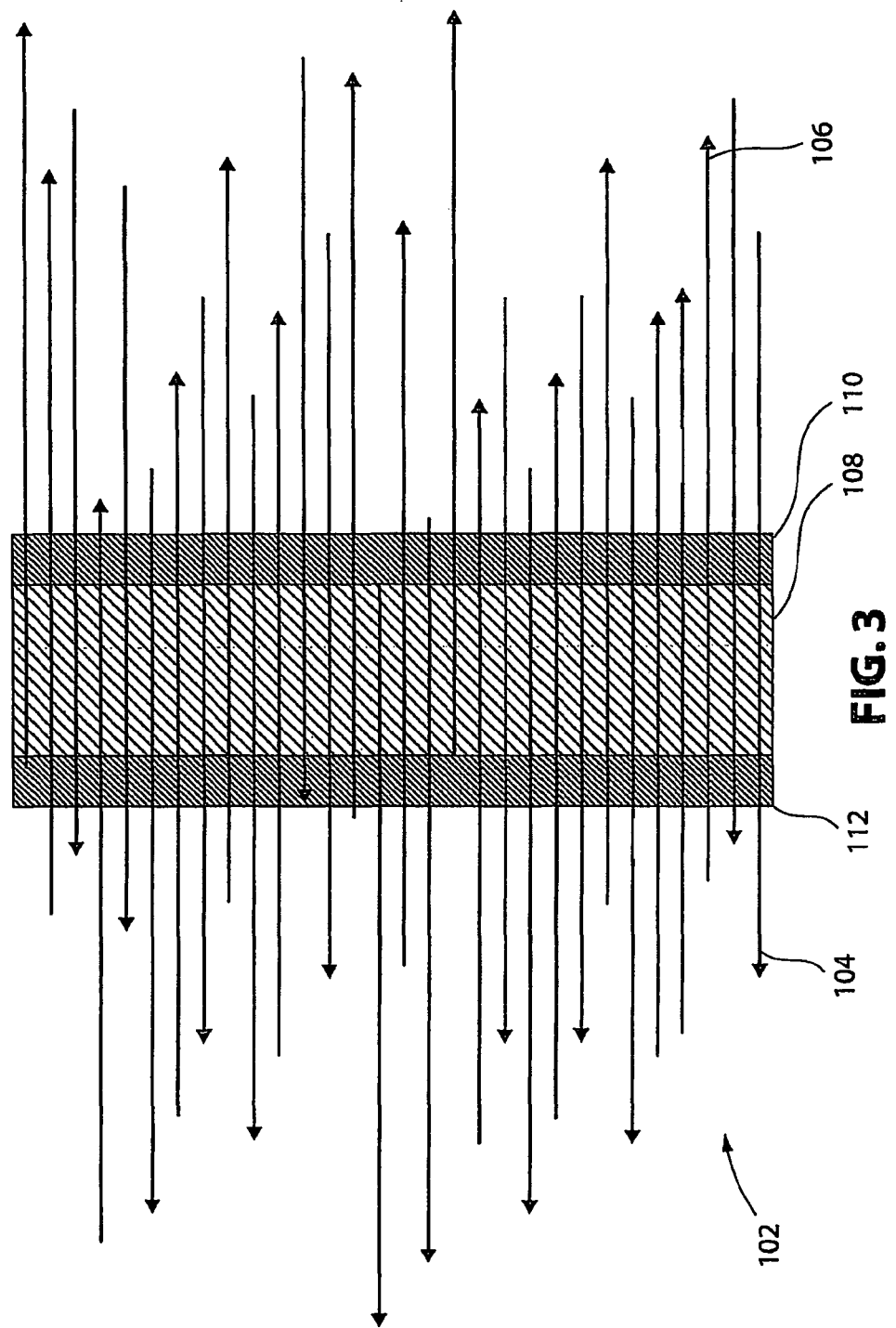
FIG. 3 is an additional exemplary embodiment of the method of the invention.

FIG. 2 is a cluster of reads 102 having a fragment read 104 and a fragment read 106. The cluster of reads 102 has a common anchor 108 that can form indices in an index. FIG. 3 shows the cluster of reads 102 and anchor sequence 108 further having primary shoulders 110 and 112. The primary shoulders 110 and 112 are the four nucleotides directly upstream and downstream of anchor sequence 108. The software can set the number of nucleotides of shoulder sequences. In a preferred embodiment, the software can have from 2 to 30 length shoulder sequences. The software can also store a default, for example, 12 for shoulder length.

Figure 4:
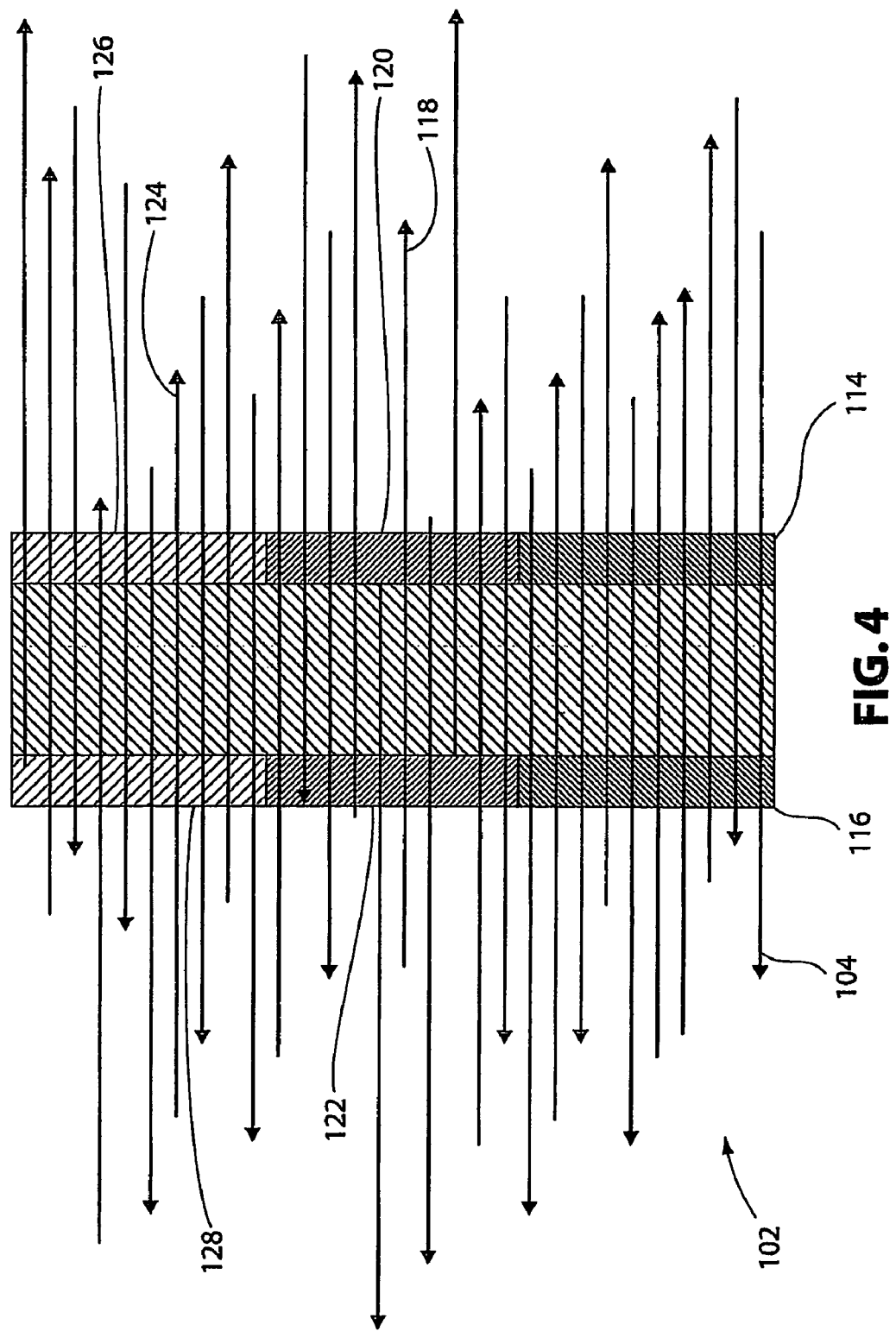
FIG. 4 is an additional exemplary embodiment of the method of the invention.

In FIG. 4, the cluster of reads 108 can include a fragment read 104 having primary shoulder regions 114 and 116; fragment read 118 having primary shoulder region 120 and 122; and fragment read 124 having primary shoulder regions 126 and 128. The fragment reads in FIG. 4 are illustrating the differences between primary shoulders that can be used to further refine a grouping of the fragment reads. In this case, there is three different groups of the original cluster of reads 102. Each of these groups can be stored independently in a file for consolidation.

Figure 5:
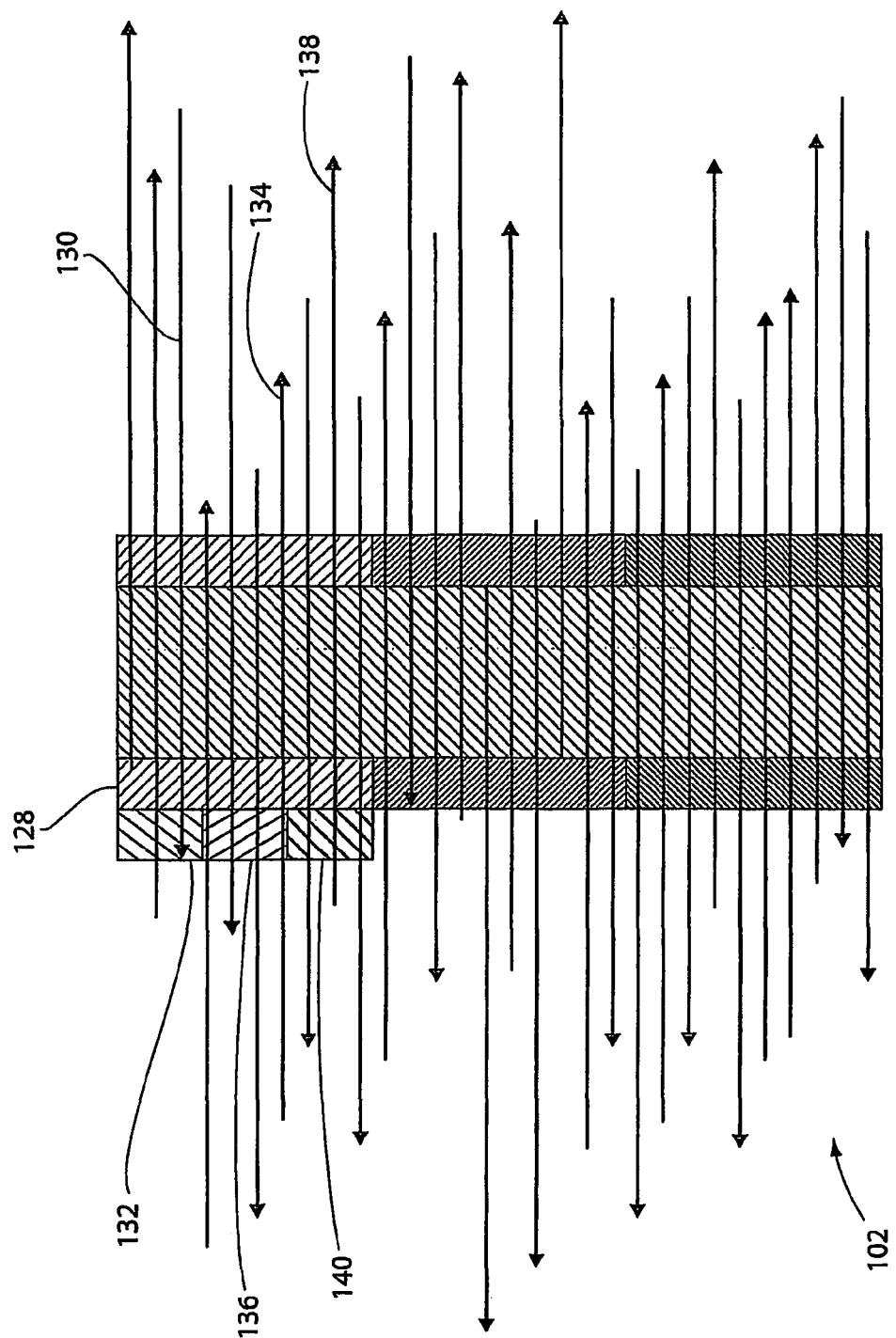
FIG. 5 is an additional exemplary embodiment of the method of the invention.

FIG. 5 is the original cluster of reads 102 having fragment read 130 and primary shoulder 132; fragment read 134 and primary shoulder 136; fragment read 138 and primary shoulder 140. The primary shoulders 132, 136, and 140 are an additional four nucleotides outside of the primary shoulder 128 that was illustrated in FIG. 4. This is extending the matching bases. Within a cluster of reads 102, the twelve base anchors are identical and within a group containing the same four base primary shoulders on either side, you have twenty bases that are identical. Therefore, the next four bases to the left and right of this group can be used to subdivide for similarity. If they are not similar, they can be used to further subdivide into another set of subgroups.

Figure 6:
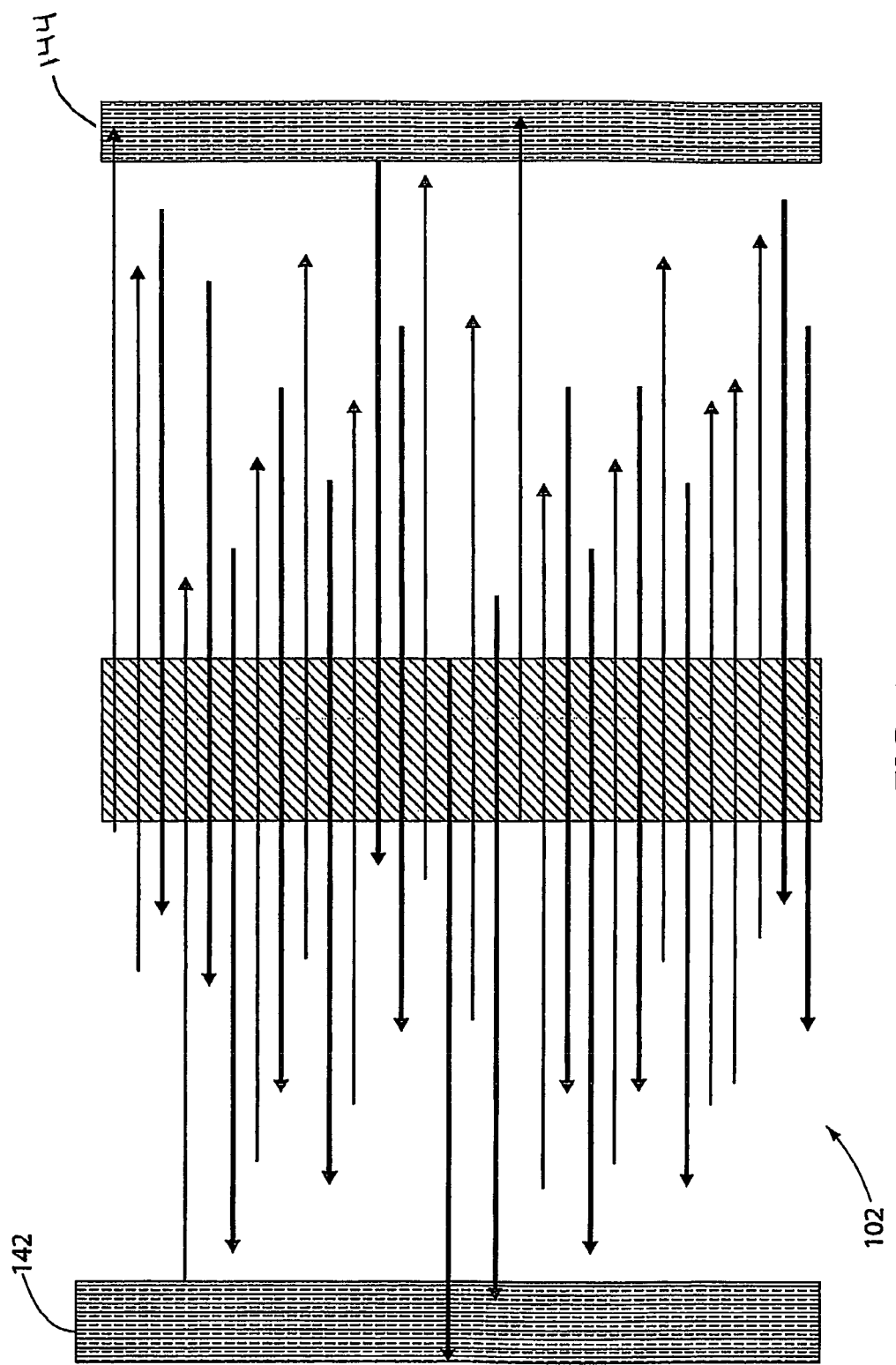
FIG. 6 is an additional exemplary embodiment of the method of the invention.

In FIG. 6, the cluster of reads 102 is shown illustrating the 5' end towards the left when the directional arrow points towards the right and the 5' end towards the right when the directional arrow is pointing towards the left. Areas 142 and 144 are not statistically reliable when the base or 3' end is present in these areas because the 3' end is the low quality end of the read. In FIG. 6, no fragment reads in the opposite orientation are included in these positions. Therefore, these nucleotides can be omitted from the consensus sequence. Consolidation of forward for left and reverse for right are more reliable at their 5' end which is on the left-hand side of the cluster. Reverse samples are more reliable on their 5' end which is on the right-hand side of the cluster.

Figure 7:
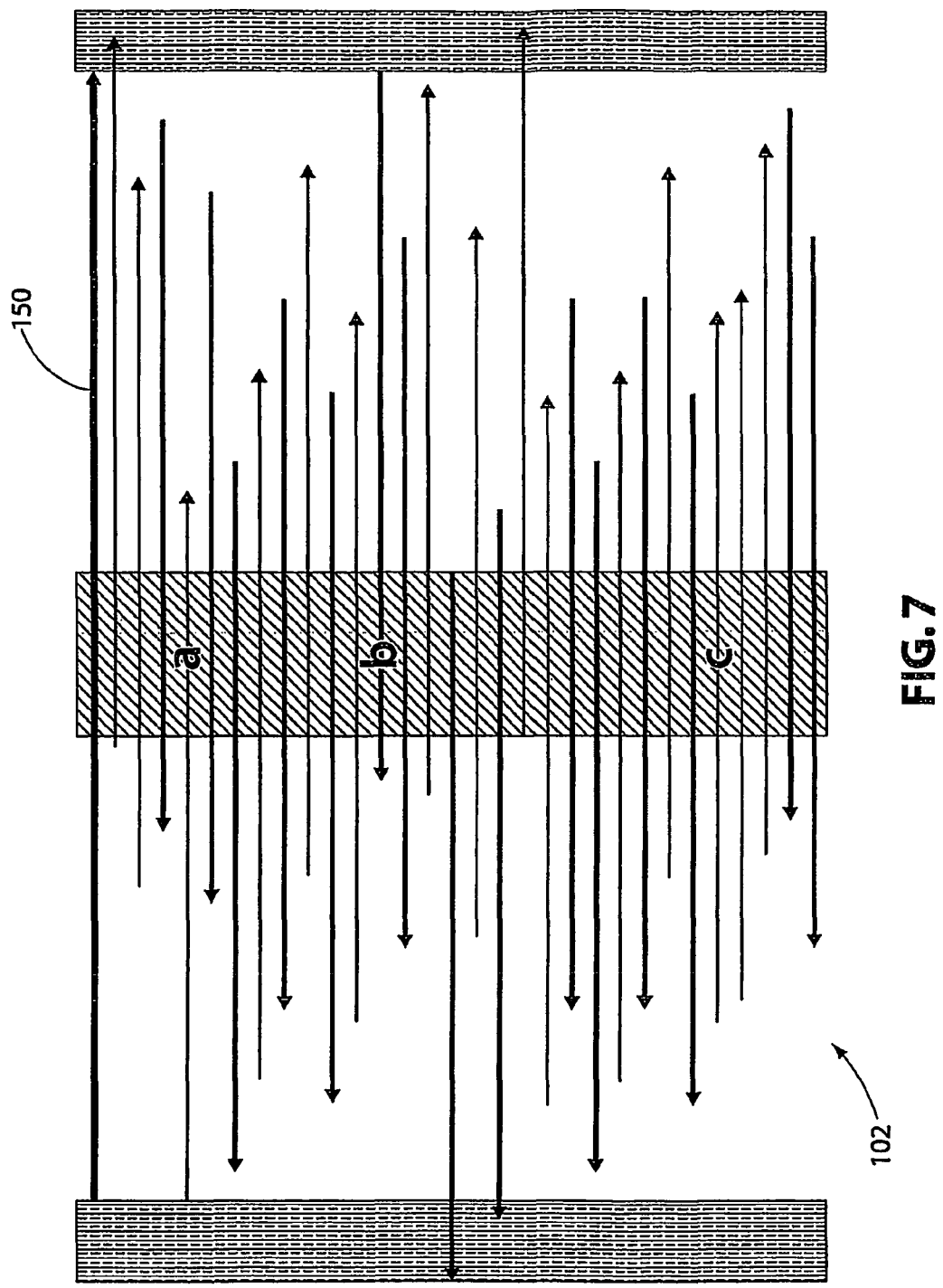
FIG. 7 is an additional exemplary embodiment of the method of the invention.
Figure 8:
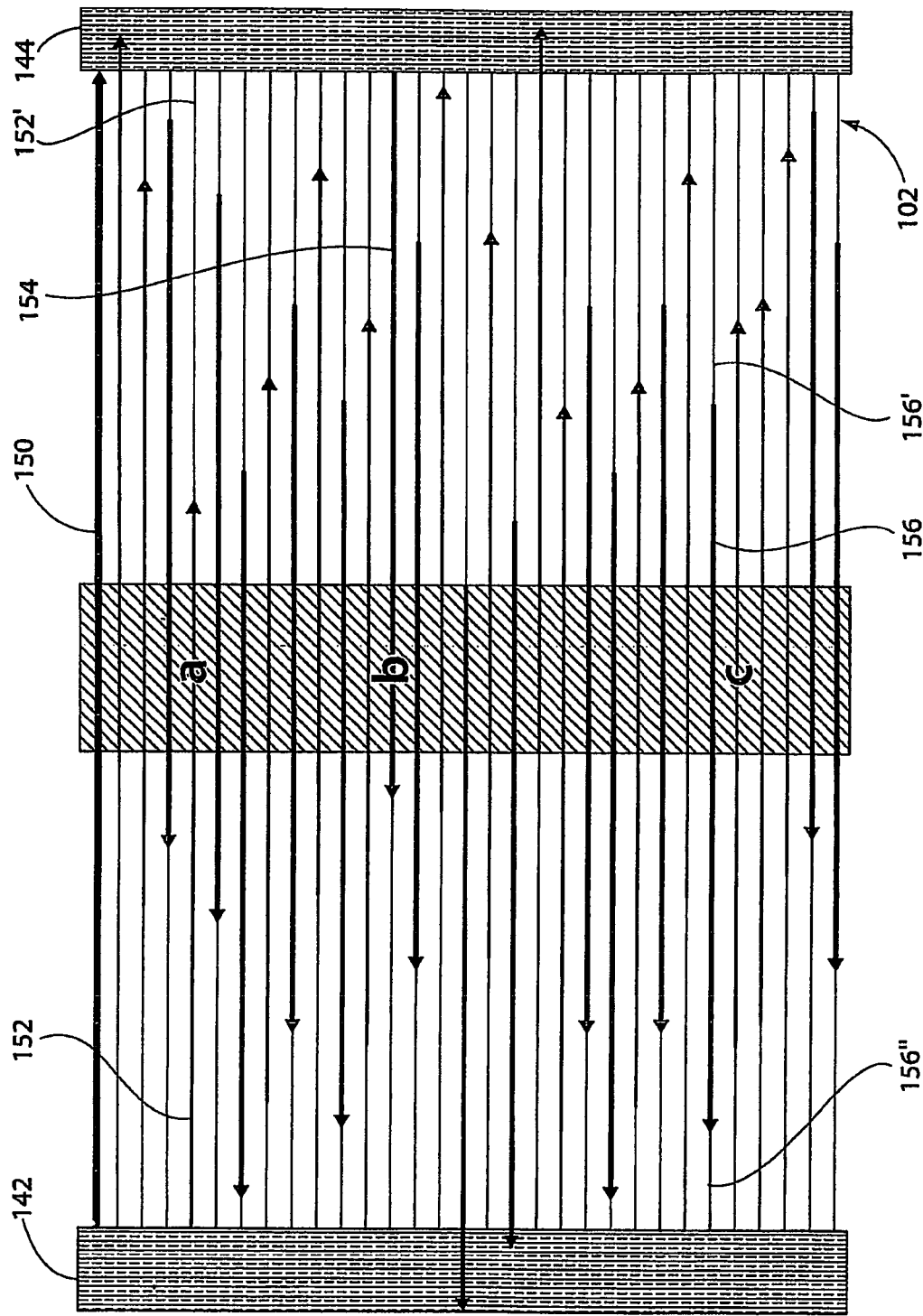
FIG. 8 is an additional exemplary embodiment of the method of the invention.

With reference to FIG. 7, the original cluster of reads 102 is shown having a consensus sequence 150. The consensus sequence 150 is the result of consolidating cluster of reads 102. As is shown in FIG. 8, the consensus sequence 150 includes only the anchor sequence and the shoulder sequences that are reliable. The areas 142 and 144 are not included in the consensus sequence 150. The consolidation of the cluster of reads 102 is creating one consensus sequence from all of the reads and many of the reads are also used in many other indices, making the consensus sequence 150 useful in resource management because it requires less memory, less storage space, and less processor time. However, the consensus sequence 150 can complicate other applications, in particular, pair reads and assembly. Multiple cycles of condensation also complicate expression studies. Therefore, the use of condensation has a further benefit because it can lengthen the original fragment reads from the cluster of reads 102. For example, fragment read 152 labeled A; fragment read 154 labeled B; and fragment read 156 labeled C, are all elongated using the consensus sequence 150. As is shown in FIG. 8, fragment read 152 A includes an area 152' that has been added to the original fragment read 152 to create an elongated fragment read. The elongation can take place on the upstream or downstream side of the original fragment read. For example, fragment read 156 C includes regions 156' and 156" to form an elongated fragment read 156. Elongation will help in consolidation where scores are low because the consensus might cause condensed reads to be truncated rather than keeping the possible correct mers of an individual read. This will help with identifying Indels and single-nucleotide polymorphism (SNPs).

Figure 9:
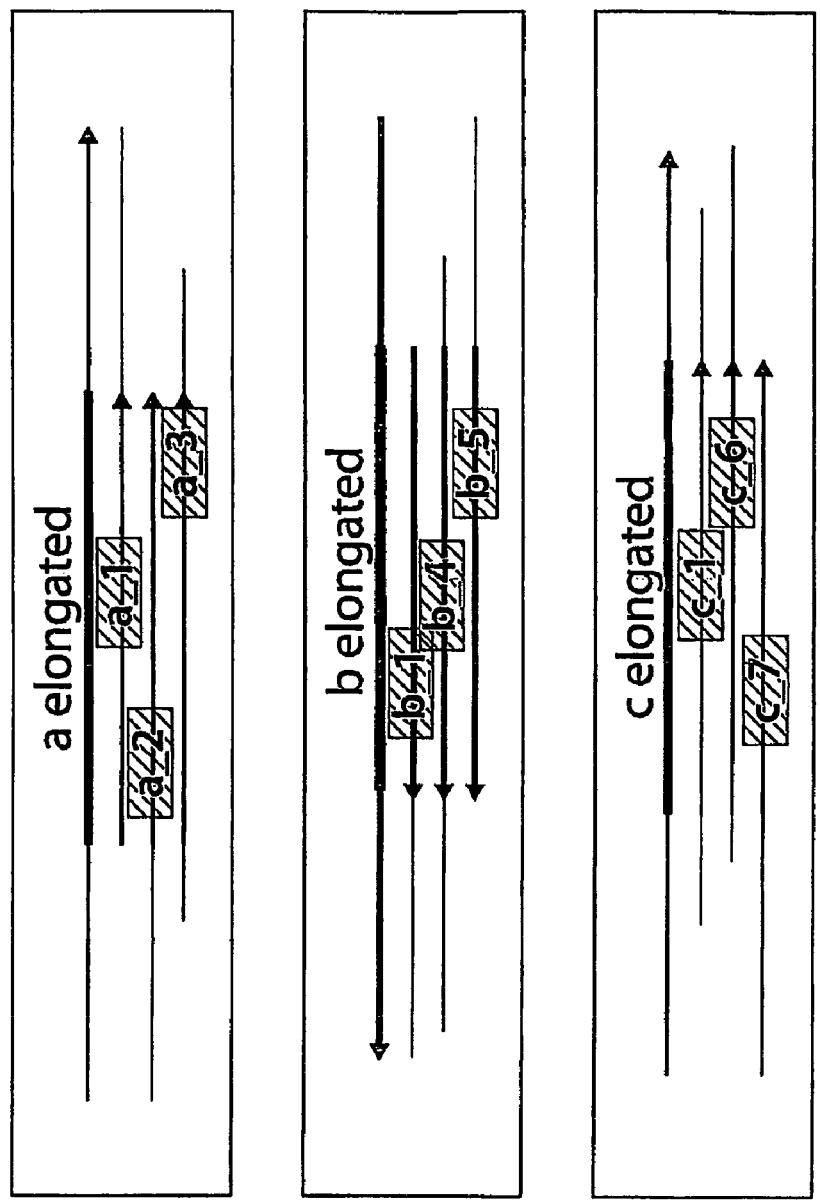
FIG. 9 is an additional exemplary embodiment of the method of the invention.

With reference to FIG. 9, the use of condensation is shown for elongating A, B, and C (152, 154, and 156). Fragment read A has been elongated using regions formed during the condensation process. Region A1 was formed during condensation and has been added to regions A2 and A3 that were formed in separate condensation processes having separate anchor sequences forming indices therein. To generate the elongated region A, three consensus sequences A_2, A_1, and A_3 formed from the individual fragment read for A have been combined. In addition, fragment reads B and C have also been elongated as shown in FIG. 9. In FIG. 9, fragment reads A, B, and C each were condensed in index 1 as indicated by A_1, B_1, and C_1, however they are located in different regions of their respective fragment reads as shown. One elongated read can be output for each original read that is input. Some reads can be elongated and corrected due to condensation while others may be unaffected because they are not condensed.

Figure 10:
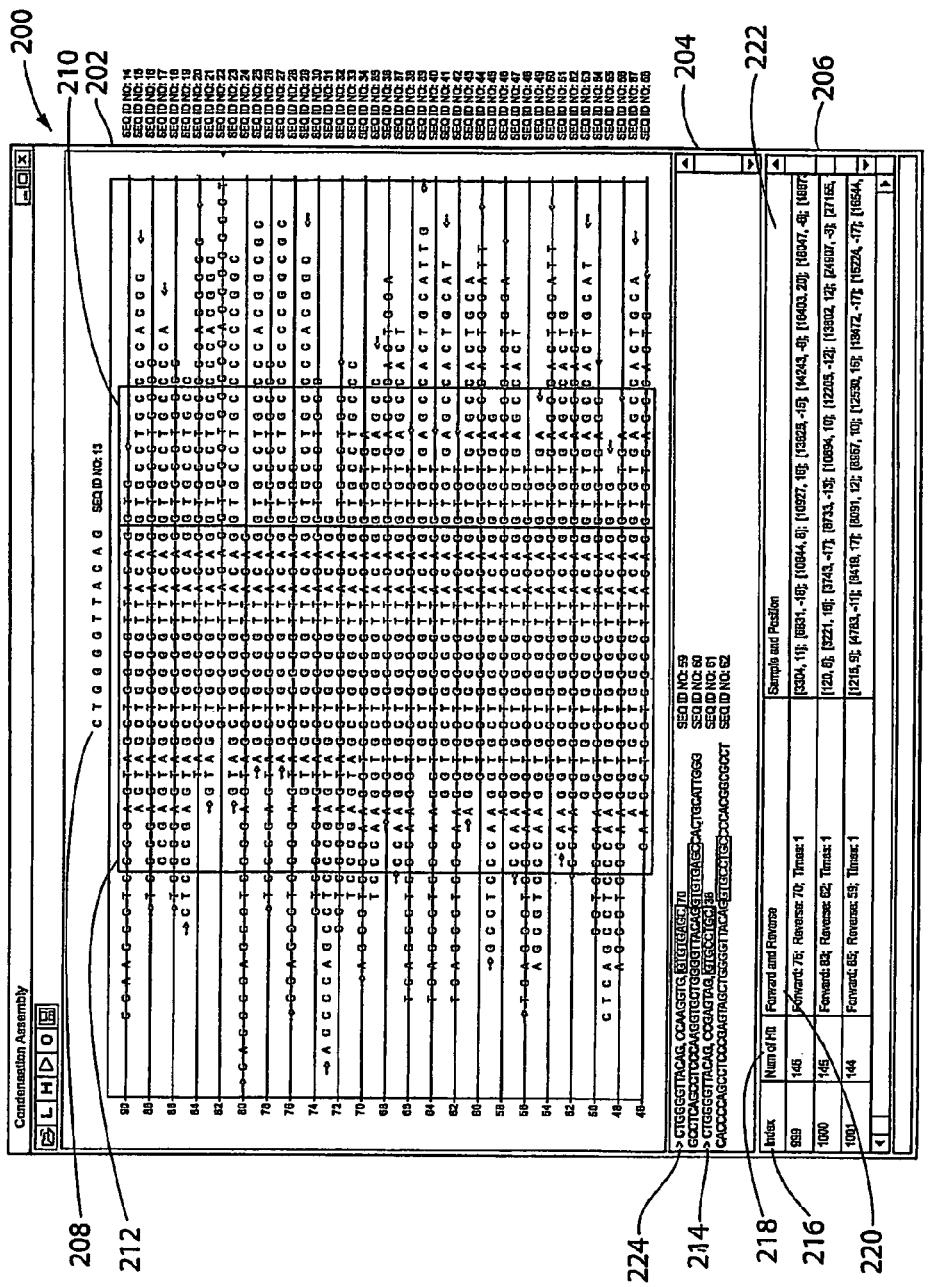
FIG. 10 is an exemplary sequence analysis window of the method and system of the invention.

With reference to FIG. 10, a condensation assembly window 200 is shown. The condensation assembly window 200 can include an assembly pane 202, a consensus pane 204, and an index pane 206. The assembly pane 202 of condensation assembly window 200 shows a grouping of fragment reads and further includes an anchor sequence 208, the anchor sequence 208 can be seen throughout the grouping of fragment reads in assembly pane 202. In addition, the homologous shoulder sequences 210 and 212 can be included in order to display the properties of the fragment reads. In assembly pane 202 outside on either the upstream or downstream side of the shoulder sequences 210 and 212 are additional nucleotides that do not fall within a consensus shoulder sequence. However, results shown in the consensus pane 204 for fragment reads having anchor sequence CTGGGTTACAG 208 (SEQ ID NO: 2), can include showing for anchor sequence having shoulder sequences 210 and 212 a consensus sequence of 214 as the result. In the index pane 206, the index number 216 of the anchor sequence 208 is shown. In addition, the number of hits 218 can identify how many fragment reads are included where that index was found. The forward and reverse 220 can allocate the number of forward and reverse hits for the anchor sequence. Sample position 222 displays the exact number of the fragment read and location therein where the anchor sequence is found. In addition, the consensus pane 204 displays the subgroups of the main group of fragment reads that was initiated using the initial anchor sequence. Therefore, subgroup 224 is the first group and subgroup 214 is the second group, each being distinguished by their outlying shoulder sequences.

Figure 11:
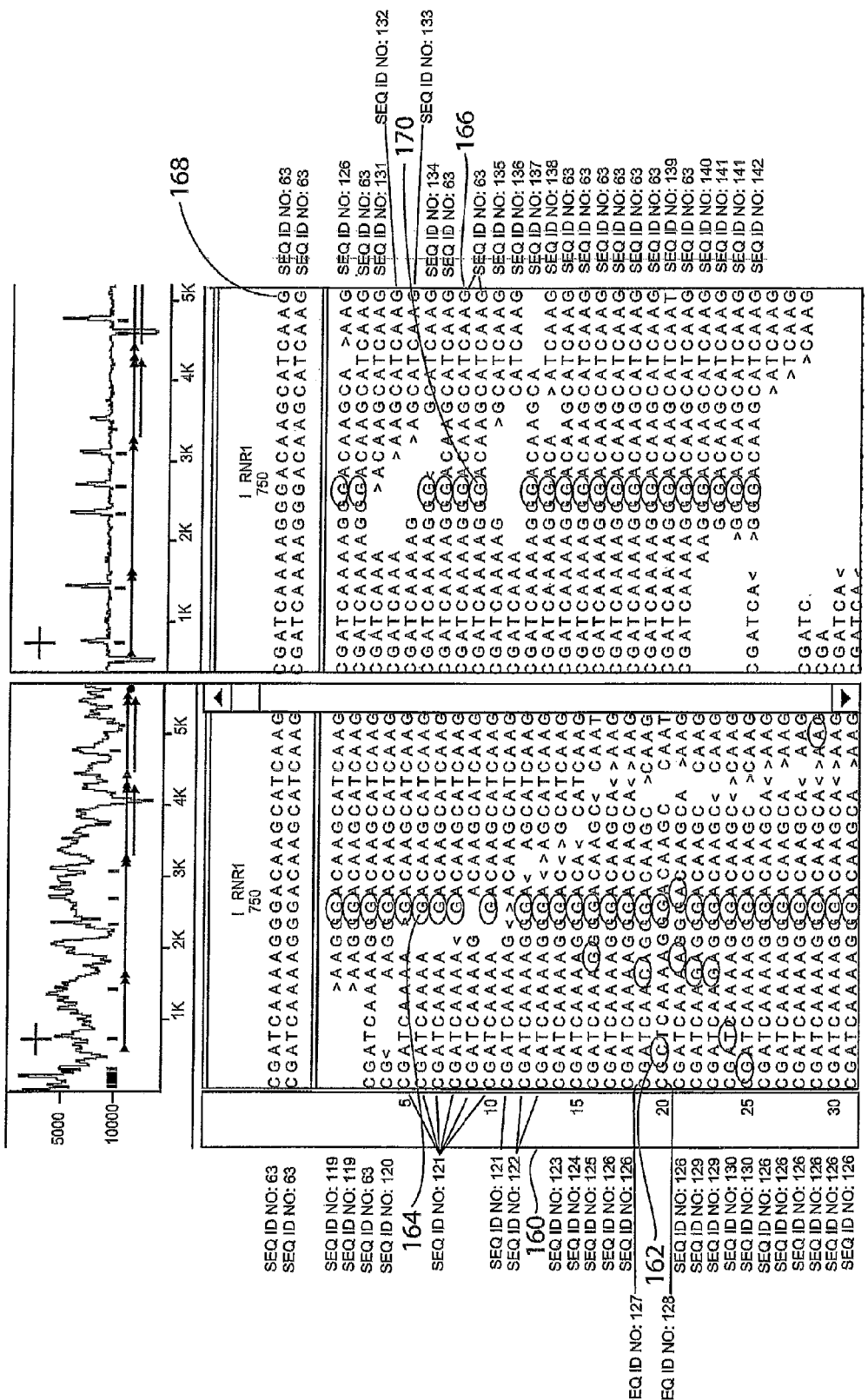
FIG. 11 is an additional exemplary sequence analysis window of the method and system of the invention.

With reference to FIG. 11, results following the use of the condensation tool are shown. The results can increase read lengths by twice the original length and can remove low frequency errors while two variations are maintained. With an original case of 5 million reads having 35 base length and 93% matching, there is a 50 base coverage and a very high false positive rate. After condensation of the original 5 million reads, the results are lowered to 2.5 million reads and a 58 base length. Condensation increases the matching to 98% and also gives 40 base coverage and substantially lowers the false positive rate.

With further reference to FIG. 11, in the first window 160, reads are aligned to the reference. In a preferred embodiment, highlights (not shown) can indicate low frequency errors 162 highlighted in gray, while mutation calls 164 can be highlighted in blue in window 160. In window 166, condensed reads are aligned to the reference shown in window 168. Low frequency errors which can be caused by instrument errors.

Figure 12:
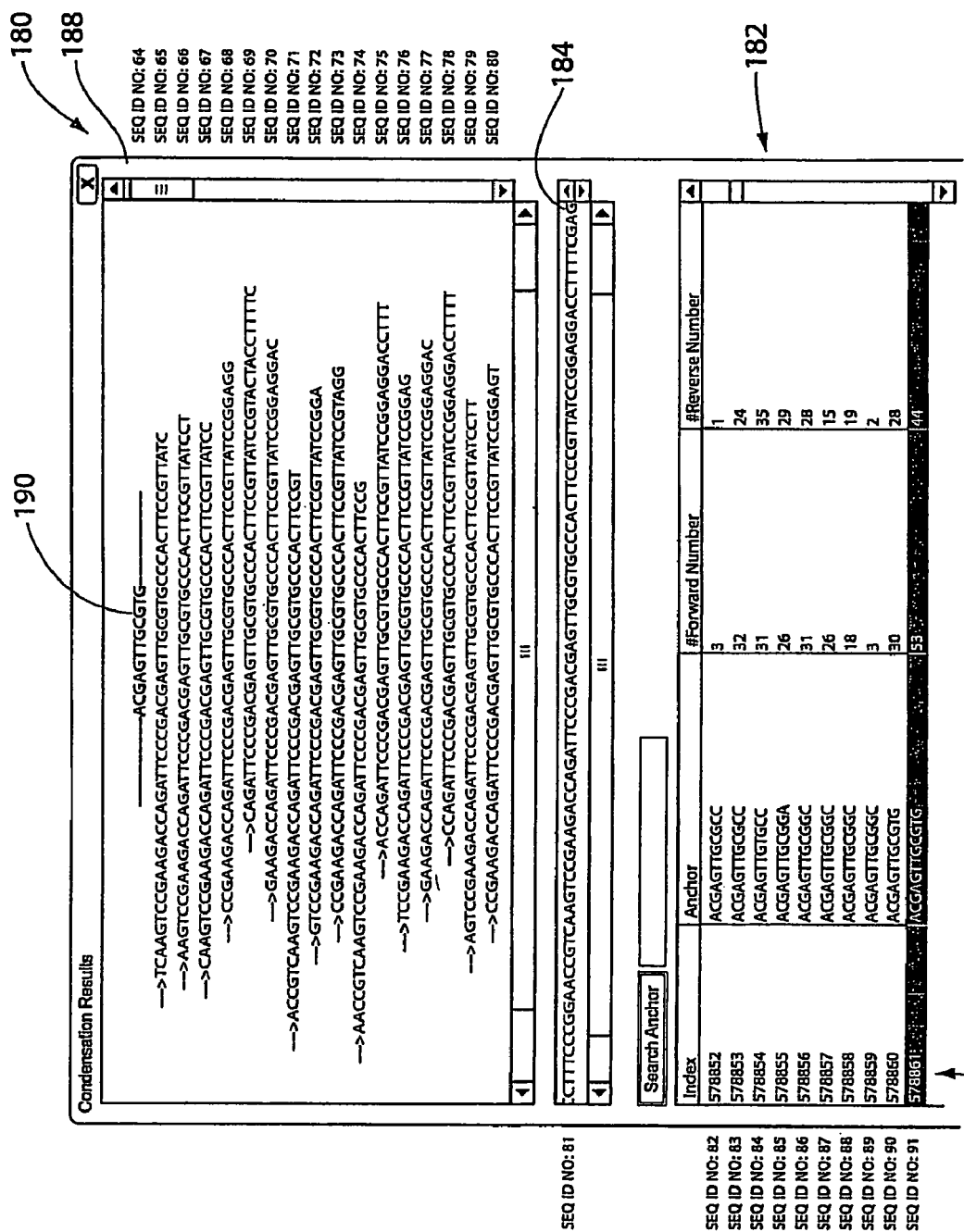
FIG. 12 is an additional exemplary sequence analysis window of the method and system of the invention.

With reference to FIG. 12, condensation results display 180 shows an index table 182 in the bottom pane. Clicking on any index in the table 182 displays a consensus sequence 184 for that index 186 above the index table 182 with all of the reads in the group shown in the fragment reads grouping pane 188 lined up beneath the anchor sequence 190. After the reads are statistically polished, many of the errors have been removed. Table 182 also shows the count of fragment reads both forward and reverse at a particular index.

Figure 13:
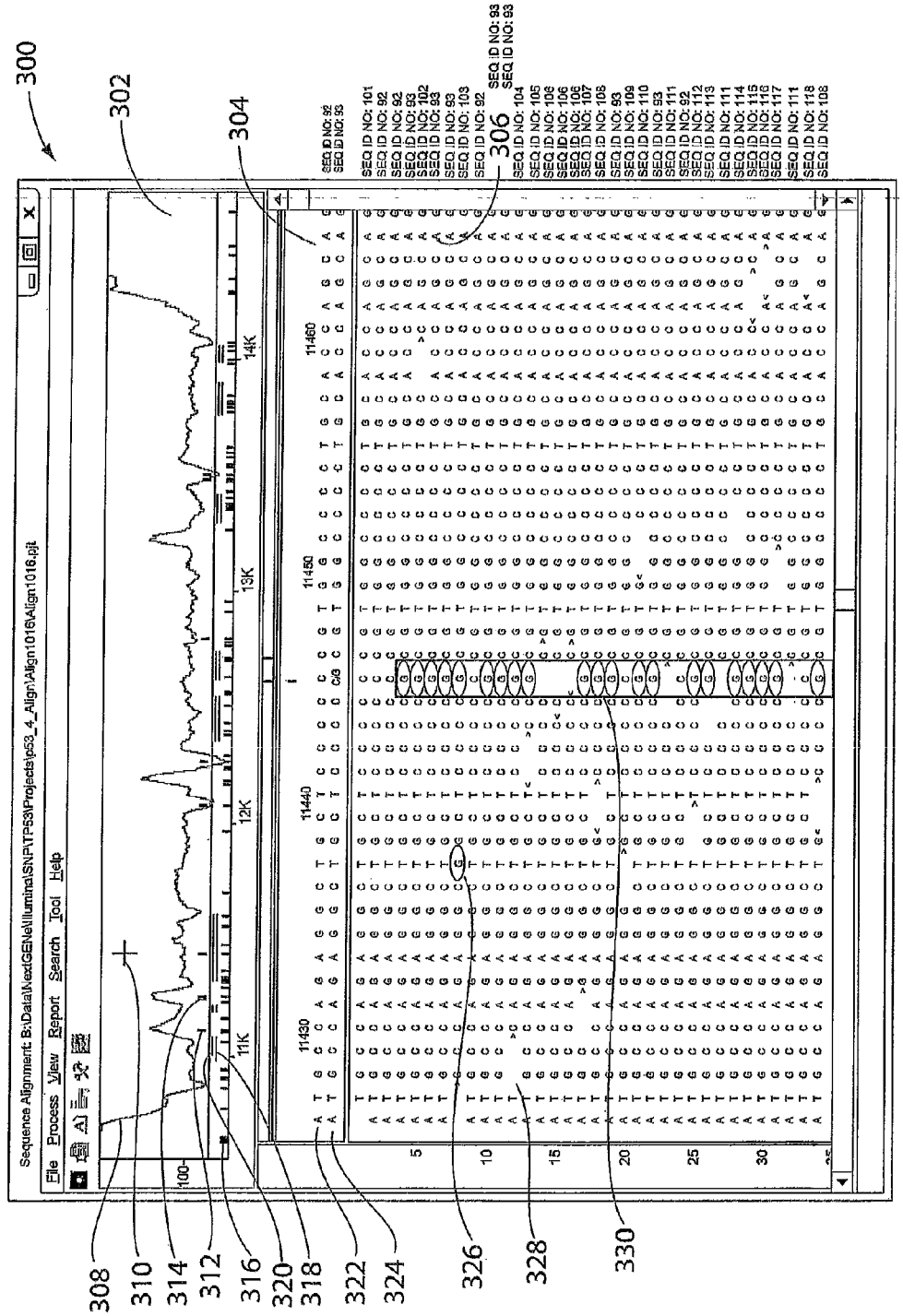
FIG. 13 is an additional exemplary sequence analysis window of the method and system of the invention.

With reference to FIG. 13, a sequence analysis window 300 includes a position pane 302, a reference pane 304, and a fragment pane 306. Position pane 302 shows a graphical representation of sequence coverage 308 and includes a position indicator 310. In addition, the position pane 302 includes indicators 312 and 314 showing instances of SNPs found and SNPs reported, respectively. The indicators 312 and 314 can use different colors to highlight the different detections, or other methods known in the art. The position pane 302 further includes indicators 316 showing SNPs reported by GEN-BANK®, indications of mRNA 318 and CDS regions 320, which also can be indicated using color for the different aspects of the layout and to highlight the different indicators. Sequence 304 includes the reference sequence 322 and the consensus sequence 324 shown. The fragment pane 306 can indicate base calling error 326 by highlighting or bolding or graying the background of the character. Arrows 328, as shown in the fragment pane 306, indicate direction. The arrow is at the 5' end of each read and points downstream to the 3' end. SNPs shown in the region 330 can be indicated using color backgrounds in addition to other methods known in the art as this is not meant to be limiting to the invention. The sequence coverage 308 can display the whole genome view with the regions indicating depth of coverage. With the region of the aligned sequence reads, mutation calls of known SNPs are shown in the region 330, while novel SNPs are relayed having a different color or other mode. A know substitution is observed at position 11446 where region 330 is aligned. The gene name can be shown in addition to the position of the indicator 310 within the whole genome view. The indicators, as discussed previously, indicate locations of known SNPs and also indentify the location of novel SNPs. The amino acid sequence is shown beneath the nucleotide sequence and an amino acid change is shown for position 1145. This alignment tool is designed to match the sequence reads to a user defined reference sequence. Multiple methods, including BLAST (or BLAT) and SOFTGENETICS® alignment methods, are available for aligning the reads to the reference. Once the references have been aligned, SNPs and Indels are highlighted for quick identification. Interactive reports explaining the variations and statistics can be produced and exported. The alignment takes place after the condensation tool is used to polish and lengthen the short sequence reads into fragments of manageable size and improved accuracy. The short reads, such as those from the ILLUMINA™/SOLID™ Genome Analyzer system are often not unique within the genome being analyzed. By clustering fragment reads, the alignment becomes efficient.

Figure 14:
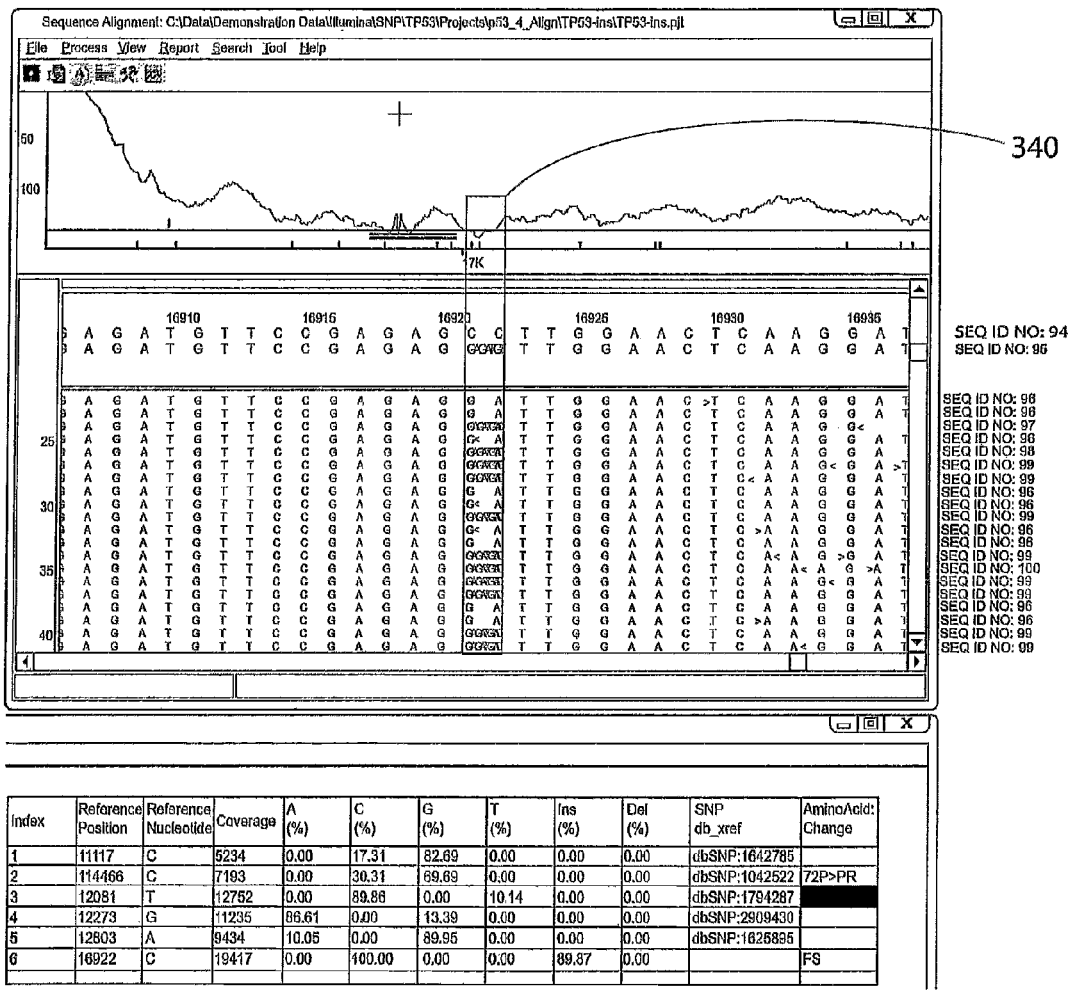
FIG. 14 is an additional exemplary sequence analysis window of the method and system of the invention.

FIG. 14 is a sequence analysis window 300, similar to FIG. 13, highlighting Indel detection. The Indels are located at region 340.

With reference to FIG. 15, a mutation based on the results shown in FIG. 14 is displayed in mutation report window 400. Mutation report window 400 can include outputs for index 402, reference position and reference 404, reference nucleotide 406, coverage 408 at the position, nucleotide coverage statistics 410A, 410C, and 410G, SNP identifying link to NCBI 412, amino acid change 414, Indel detection indicator 416, and change of coverage at the position. The mutation report shows the list of all of the variations marked as mutation calls. Mutation calls can be manually reviewed and the report allows for calls to be edited, deleted, or added. Mutation calls within this report are organized by position within the reference, and each line contains a position within the reference, the reference nucleotide coverage and percentages; for each allele found, percentages of reads containing Indels, amino acid changes, gene and/or chromosome location, and DB SNP identification. Several charts are also displayed in the mutation report. Chart 418 graphs the reference nucleotides and their expected percentages. Chart 420 graphs the percentages for all nucleotides at each position. Chart 422 graphs the gain and/or loss of each allele. Genotype is included to indicate whether mutations are heterozygous or homozygous. Mutation calls show what type of information is observed. Amino acid change is also shown for mutations and coding regions. The sequence assembly system of the present invention includes programming instructions operable to provide options to optimize results for a sequence assembly project.

Figure 16:
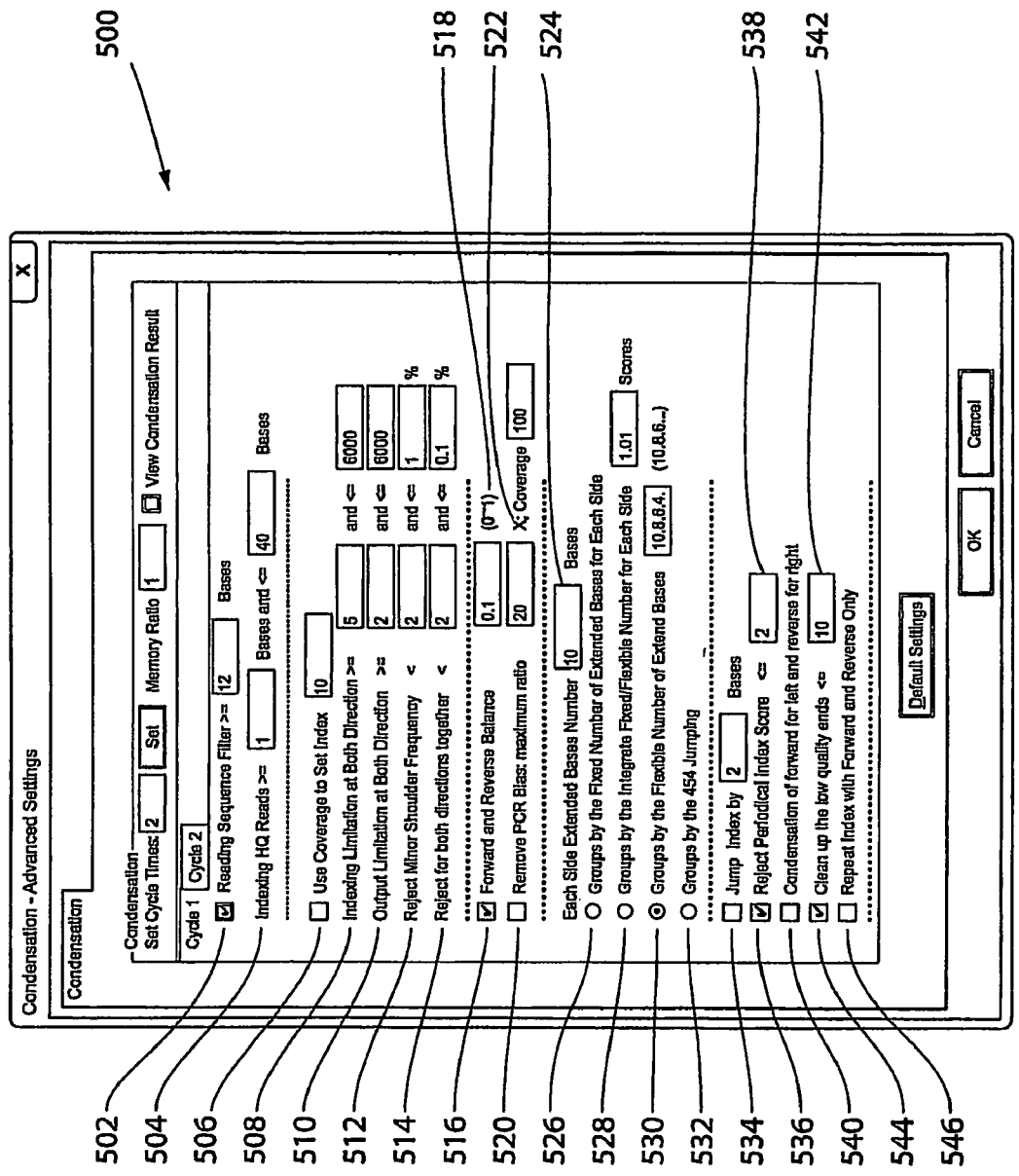
FIG. 16 is an additional exemplary sequence analysis window of the method and system of the invention.

With reference to FIG. 16, the setting options for a project are shown. The options include control of the sequence assembly system, they can be stored in memory or storage, and are operable by the processor to control count requirement settings that index the anchor sequences, settings to control forward and reverse balance, settings for indexing the anchor flanking shoulder sequences in terms of size and number, and also settings for scoring the 5' and 3' ends of fragment reads. Advance setting window 500 includes setting 502, having a check box for indicating that a reading sequence filter should be used, the reading sequence filter is set in a text box, shown as 12 in advanced settings window 500. Setting 504 is for indexing HQ reads and includes text boxes to indicate a range, shown as ranging between 1 and 40 bases in FIG. 16. Setting 506, having a check box to indicate that a coverage should be used to set the index, is used for high coverage sequences. When a very high coverage, for example 10,000 sequences are present, it can be desired to have an index limitation in both directions. The setting 506 includes a text box to indicate the index limitation, shown as 10 in FIG. 16. Setting 508 and setting 510 provide a range for minimizing a number of fragment reads. Setting 508 is for limiting the index in both directions, as shown, between 5 and 6,000. Additionally, settings 508, or any of the settings, can have a "−1" which indicates this setting is not observed. Setting 510 is similar to setting 508 with the requirement, however, that each direction have an output in the range of the provided numbers, as shown, between 2 and 6,000. Index and output limitations are provided because if too few counts are found, errors in the fragment reads could be included in the sequence assembly system and if too many counts are provided, then a PCR primer can be left over. Settings 512 and 514 are related to the subgrouping fragment reads based on the homologous flanking shoulder regions. Setting 512 indicates to the sequence assembly system that minor shoulder frequencies can be rejected, those where fragment reads covering two shoulders are less than 2 counts or less than or equal to 1% of the fragment reads. For example, the group is therefore rejected if there are less than the number of bridge reads required, where a bridge is a fragment read having full coverage, including the anchor and two shoulders. SEQ ID NO: 104 in FIG. 2 meets the requirements to be considered a bridge read, while the first read in FIG. 2 does not meet the requirements. Setting 514 provides options to reject a subgroup if the number of each subgroup is not within the provided range, in this case if the subgroup has less than 4 counts or is less than or equal to 0.1% of all the counts in the index.

With continuing reference to FIG. 16, settings 516, 518, and 522 are related to directional limitations. Setting 516 includes a check box to indicate if forward and reverse balance should be used. Setting 518 indicates a total percentage that must be met, if the forward and reverse balance check box is selected, a number of counts of forward or reverse are divided by the total number of fragment reads which gives a number which must be greater than setting 518. Setting 520 includes a text box which indicates to remove PCR bias. Setting 522 gives a maximum ratio and a coverage number shown as 20 for the maximum ratio and 100 for the coverage. If setting 520 is selected, then the reads will be sorted into two files having reads without bias and reads with bias.

With continuing reference to FIG. 16, settings 524, 526, 528, and 530 are for indicating groupings. Setting 524 includes a text box to store a shoulder sequence length requirement for extending each side's base number which is the length of the shoulder for each side. Setting 526 is for grouping, by a fixed number, by extended bases for each side. In setting 526, the user selects the base in setting 524 for the two shoulder sequences. Setting 528 is the group by the integrate fixed/flexible number option for each side. Setting 528 can select a number of shoulders with a length of 10 bases as specified by setting 524 to sort into sub-groups, based on difference toleration. The sequence assembly system can separate the reads into many tertiary groups if reads are different from the consensus. The setting 528 includes a difference toleration text box shown set to 1.01 which indicates to the software program to sort fragment reads into sub-groups if there is a 2 base difference. When using difference toleration, the shoulders are the same, but there is a difference is in the other common regions. Setting 530, a radio button is provided to indicate that groups are made from the flexible number of the extended bases, giving the option to dynamically change the shoulder size from 10 to 8 to 6 to 4, starting with 10 and depending on the fragment reads if they include 10 bases; otherwise, they will go from 8 then to 6 then to 4 bases. Setting 532 is for groups by the 454 Jumping Rule. Setting 532 provides the option to include shoulders that are not in the neighborhood of the anchor sequence if the shoulders are at their homopolymer shoulder sequences between the shoulder sequence and the anchor sequence. The shoulders are only a few bases away from the anchor. Jump index 534 can be selected to indicate distance used between next and previous shoulders having homopolymers in between. The jump index is for reduction of calculation. The jump index is used to avoid the error region having homopolymers. When set to 2, the difference between the shoulder and the end of the anchor sequence must be at least two bases, otherwise the next index will be used as the shoulder. When an index is used, the next index can be skipped by moving one base to the right. Setting 536 has a check box to indicate that periodical index scores can be rejected. Periodical index score at setting 536 is a scoring system to catch repeat sequences such as AAAAAAAAAACG (SEQ ID NO: 3) or ACACACACACAC (SEQ ID NO: 4) which can be problematic and the software does not need to calculate them. The same nucleotide score enabling deducts ⅜ for AA, ⅖ for ACA, and ⅛ for ACGA. For each nucleotide, both sides are considered. The score cannot be negative. Therefore, for sequence:

AAAAAAAAAACG A A A A A A A A A A C G AAAAAAAAAACG (SEQ ID NO: 5)

⅛×10 0 0 00 0 0 0 1 8 8

The total score is: (1+1+8+8)/8=2.25.

This means that the two nucleotides are meaningful based on the periodical index score being less than or equal to one for rejections. Setting 540 indicates condensation for forward in the left direction and reverse for the right direction, therefore the consensus sequences are only taken from the 5' and anchor sequences and the 3' sequences are not used to construct a consensus sequence. This is useful because 3' sequences can be error prone. Setting 544 indicates that low quality ends should be cleaned, trimming the ends if the quality is poor. For example, if the quality score 5' end nucleotide is 7 and the quality score of the 3' end nucleotide is 2, and there are two reads, one forward read and one reverse read, if coverage in nucleotide is A, the same call, the score is 9 which is calculated by adding both quality scores of 7 and 2. However, if the forward call is A and the reverse call is G, then the consensus will be A with a score of 5 which is calculated by subtracting 2 from 7. Setting 546 has a check box to indicate repeat index with forward and reverse only to pick up reads only using repeat index and shoulder sequence using forward only or reverse only to condense the reads. A repeat sequence of $(ACAC)_N$ can cover more than 40 BPS, which is longer than the reads length of 36 BPS. Therefore, it is impossible to condense the reads for AC greater than the length of the reads. However, with setting 546, the sequence assembly system can pick up the reads only using the repeat index and the shoulder sequence forward or reverse only to condense the reads.

The 454 Jumping Rule setting 532 is used to separate reads which are known to have many errors in homopolymers. Programming instructions on the processor break the fragment reads at the homopolymer positions having greater than 2 homopolymers such as AAA, CCCCC, GGG, TTTT. The portions of the sequence without large homopolymers will be conserved. In the 454 Jumping Rule method, the anchor is greater than 12 BPS. The anchor sequences are underlined in the following example:

(SEQ ID NO: 6)
>FH0Y44002G6SGQ length = 232 xy = 2830_2568
region = 2 run = R_2008_10_01_16_37_42_
CTCGAGAATTCTGGAT<u>CCTCCGGCAGGA</u>3, 3<u>ATGAGGCAAGTC</u>3, 3CAGC3, 3<u>CTGGCCGAGGAGGAGGAGA</u>3, 3AGC3, 3<u>CATGGCCATCATA</u>3, 3<u>AGGACACAGGCTACGCG</u>4, 4<u>GCTCATGGCCTGGGTGT</u>

(SEQ ID NO: 7)
>FH0Y44002HRP0J length = 174 xy = 3069_0225
region = 2 run = R_2008_10_01_16_37_42_
CTCGAGAATTCTGGATCCTCAATCT<u>CAACTAGGTGGA</u>3, 3<u>ACTAGGCAAGGA</u>ACAGGTAGGAAGCTGAATTGGCTCGTGAGATAAC<u>CTA AGAGATATC</u>3, 3<u>CAGTGTCTATGCAGTACCTA</u><u>TTCTTGTGTACT</u>3,

3TATCT3, 3TATTCACTGGA4, 4AC3,

3<u>CTTCTACAACCA</u>CATGCA4, 4AT

The example will show the key words, CCTCCGGCAGGA (SEQ ID NO: 8) with shoulders NNNNNNNNNNNN and ATGAGGCAAGTC (SEQ ID NO: 9); keyword ATGAGGCAAGTC (SEQ ID NO: 9) with shoulders CCTCCGGCAGGA (SEQ ID NO: 8) and CTGGCCGAGGAG (SEQ ID NO: 10); keyword CTGGCCGAGGAG (SEQ ID NO: 10) with shoulders CTGGCCGAGGAG (SEQ ID NO: 10), CATGGCCATCAT (SEQ ID NO: 11); keyword AGGAGGAGGAGA (SEQ ID NO: 12) with shoulders CTGGCCGAGGAG (SEQ ID NO: 10) and CATGGCCATCAT (SEQ ID NO: 11); the pattern repeats. One read will be used multiple times in condensation. The step length is dependent on the local sequence and it is flexible. All of the reads in a group having one keyword and either or both of the shoulders will be aligned to keywords. Shoulders are found in the neighboring keywords or in the same section when the length of the keyword is long. The Indel errors are ignored. Condensation will remove any Indel and sequence errors. If there is any error in the index of keywords, this read will not be used in the condensation. The next keyword or previous keyword will most likely include the sample.

Figure 17:
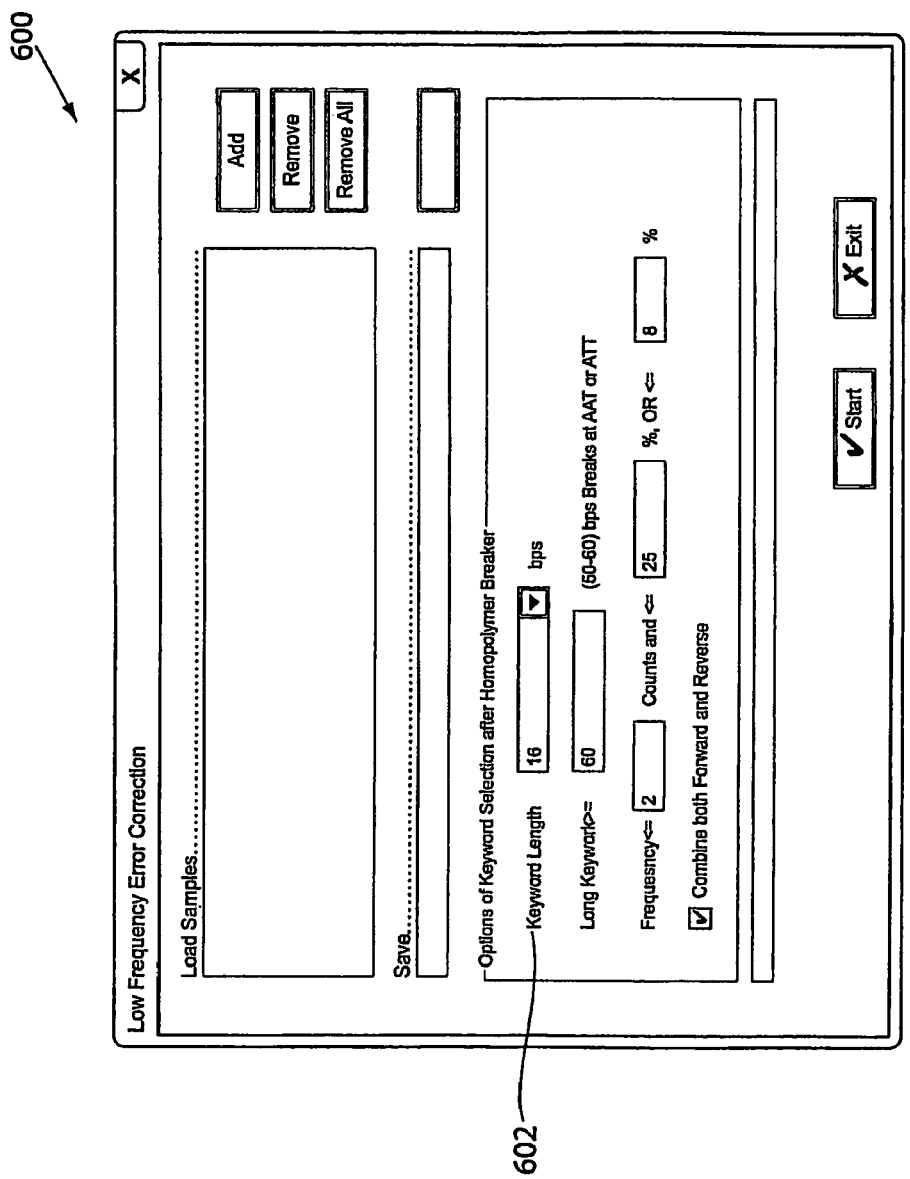
FIG. 17 is an additional exemplary sequence analysis window of the method and system of the invention.

With reference to FIG. 17, low frequency error correction of 454 Jumping Rule is discussed. Sequences of 454 reads are broken into many words and keywords for current reads and reverse complements the homopolymer number correction. First, the keyword (anchor) length 602 can be defined by the user or sequence assembly system and sets it as a default. The minimum length is 20 (16+2*2) BPS because we have at least three nucleotide in the breaking points and one BPS is included. Next, there are two numbers associated with each keyword, 1) right number of homopolymers and 2) left number of homopolymers. The sequence assembly system then sorts all of the keywords and the same keyword in different reads will be clustered. The median value of the keyword as the value of the number of homopolymers is taken from each side.

After the numbers of homopolymers are corrected, a count of the number of the keywords is conducted. The keywords are then sorted into a region containing similar sequences. If two of the sequences differ by 1 BPS and the frequency of one is less than ⅛th of the other or is only 1 and 2 counts, the low frequency keywords will be corrected to the high frequency keyword. The original sequences are modified to the new sequences. After errors are corrected, software is able to assemble three times longer than original reads.

The sequence assembly system can be used on the following three applications: Deep Sequence to quantify the rare allele frequency in human population; cDNA assembly using 6 cycles to assemble mRNA transcripts; and De novo assembly.

For deep sequence, the sequence error rate of Illumina™ reads is measured about 2%. After condensation the sequence error rate reduces to 0.1%. The sequence error reduction allows us to measure frequency of rare allele. In one example, data sets polled from 364 patients and 360 normal people from ABCA1 gene spanning 150 kb with 50 exons. Each of the two samples is measured in two lanes as replicates. About 7.2 M reads occur in each lane. The coverage is about 8000×. The replicate measurements allow to determination of the system linearity, using one normal as control and patient sample, when the frequency of all of the mutations are measured. The allele frequency is determined from the condensed reads. The numbers of raw reads associated with the condensed reads are used to determine the allele frequency. Four thousand one-hundred and eighty-three (4,183) mutation calls were made after aligning the raw reads, which is reduced to just 77 mutation calls after aligning condensed reads.

cDNA sequences are measured with ILLUMINA™ Genome Analyzer. There are about 14 million reads of 36 bps. The first cycle of condensation results 6.9M reads of 53 bps. The second cycle gives the read of about 100 bps. Software is able to generate the sequence of 1500 bps after 6 condensation cycles. We are able to assemble into 27000 mRNA transcripts.

De novo sequences with the short reads from genome analyzers produce an additional layer of complexity for assembly. The sequence assembly system, was developed to assist with these complex assembly issues. After using the sequence assembly system tools to remove low quality reads and trim low quality bases from reads in order to improve assembly accuracy and using the software condensation tool to statistically polish the short reads, correcting additional errors and simultaneously lengthening the reads, the sequence assembly system can more reliably assemble the short reads into contigs of 500 bps to upwards of 50 kbps. Additionally, the original short reads used to generate each assembled contig are recorded to show the copy number and Indel positions. The sequence assembly system is capable of detecting Indels of 1-30 bps. The sequence assembly system statistically polishes datasets of adequate coverage to remove random sequencing errors and increase read lengths. Repeating the condensation removes systematic errors and further lengthens the sequence reads with each additional cycle. The polished and elongated reads can be assembled into large contigs while removing redundant reads. Once the dataset has been cleaned to remove low quality reads and ends, the remainder of the process is fully automated through the use of software that guides through the project configuration.

As an example of de novo assembly, a sample of the K-12 DH10B strain of E. coli that was sequenced with the SOLID SYSTEM™ sequencing system was assembled using the sequence assembly system. This dataset has high quality reads suggestive of about 30× coverage. These single reads have low quality reads removed, low quality ends trimmed, and the first color-call removed from reads using the sequence assembly system. The remainder of reads, those of high quality and reliability, were processed through the sequence assembly condensation and assembly system modules to generate larger color-space contigs. Since the DH10B genome is available, the assembled results were then aligned to this genome to validate the assembly results. Four cycles of the sequence assembly system condensation were performed followed by assembly of the condensed results to generate 3220 contigs. Over 85% of these contigs were larger than 500 bps, and the largest is over 16 Kbps. The assembled contigs were aligned to the DH10B reference genome to validate the assembly results. Only three of the assembled reads did not match to the DH10B genome, indicating that the contigs produced by the sequence assembly system are very reliable. In one example, 4,024,290 bases of the 4,686,137 base genome have coverage using the sequence assembly system as described above, approximately 86% coverage. When excluding the duplicated region of this reference genome that is larger than 100 kbps, coverage is 88%.

It will be readily appreciated by those skilled in the art that modifications may be made to the invention without departing from the concepts disclosed in the foregoing description. Accordingly, the particular embodiments described in detail herein are illustrative only and are not limiting to the scope of the invention, which is to be given the full breadth of the appended claims and any and all equivalents thereof.

The invention claimed is:

1. A method for automated assembly of DNA sequence data comprising of DNA fragment reads into contiguous DNA segments using a computer system with processing and information storage capabilities, the method comprising the steps of:

entering into the computer system a plurality of DNA fragment reads;

identifying a plurality of n-mers within each DNA fragment read of a plurality of the DNA fragment reads and compiling an index of the of n-mers;

identifying one or more anchor sequences common to a plurality of the reads among the indexed n-mers; and generating a consolidated sequence using a plurality of reads comprising the same indexed anchor sequence, wherein the consolidated sequence is generated by subgrouping the plurality of reads comprising the same indexed anchor sequence according to two or more different shoulder sequences thereby producing two or more subgroups of reads and generating one or more consolidated sequences, wherein each of the one or more consolidated sequences is generated using reads of one of the two or more subgroups.

2. A method as claimed in claim 1, further including the step of elongating a selected fragment read by pooling consolidated regions of the plurality of fragment reads.

3. A method as claimed in claim 2, wherein an average read length is increased in the range of 1.4-1.6.

4. A method as claimed in claim 2, further including preservation of Indels and/or SNPs.

5. A method as claimed in claim 4, further including the step of aligning an elongated fragment read to a user defined sequence read to determine SNP and Indels.

6. A method as claimed in claim 1, in which the step of identifying a plurality of n-mers within each nucleic acid fragment of a plurality of nucleic acid fragment reads comprises identifying all n-mers within each nucleic acid fragment of a plurality of the nucleic acid fragment reads.

7. A method as claimed in claim 5, wherein low frequency errors are eliminated.

8. A method as claimed in claim 5, wherein total read count is reduced.

9. A method as claimed in claim 1, wherein consensus sequence errors are reduced below 0.5%.

10. A method as claimed in claim 1, wherein the anchor sequence has a length of 12 bases.

11. A sequence assembly system for transforming DNA sequence information from DNA fragment reads into contigs of contiguous DNA sequence, the system comprising a computer processor, memory, and data storage devices, the memory having programming instructions to operate the computer processor to consolidate a set of fragment reads by:

identifying a plurality of n-mers within each DNA fragment read of a plurality of DNA fragment reads and compiling an index of the of n-mers;

identifying one or more anchor sequences common to a plurality of the reads among the indexed n-mers; and generating a consolidated sequence using a plurality of reads comprising the same indexed anchor sequence, wherein the consolidated sequence is generated by subgrouping the plurality of reads comprising the same indexed anchor sequence according to two or more different shoulder sequences thereby producing two or more subgroups of reads and generating one or more consolidated sequences, wherein each of the one or more consolidated sequences is generated using reads of one of the two or more subgroups.

12. A system as claimed in claim 11, further comprising using said computer processor to output to a display a user interface window, said window further displaying one or more of a whole genome pane, an aligned sequence pane, and a consensus sequence pane.

13. A system as claimed in claim 11, further comprising using said computer processor to output to a display a user preferences window, said preferences including choices to programmatically control said processor of said assembly system with rules, said rules comprising:

Counts Selection Rules;
Directional Limitations;
Shoulder Selection Rules; and
jumping rules.

14. A system as claimed in claim 13, wherein the rules include an anchor sequence dynamically adjustable.

15. A system as claimed in claim 14 wherein a 5' end is given more statistical weight than a 3' end of the fragment reads.

16. A system as claimed in claim 11, further comprising jumping rules, said jumping rules comprising slicing the plurality of DNA sequences into multiple sections wherein at least one section includes an at least 12-mer fragment and the DNA sequences are sliced at positions having greater than 2 homopolymers, and conserving a portion of the DNA sequences without large homopolymers.

17. A system as claimed in claim 11, further including programming instructions operable to calculate a known Indel by aligning the consolidated sequence or an elongated version thereof having an anchor sequence with a known reference sequence having the anchor sequence to determine the Indel location.

18. A system as claimed in claim 11, further including programming instructions operable to calculate a known single-nucleotide polymorphism (SNP) by aligning the consolidated sequence or an elongated version thereof with a known reference sequence to determine the SNP location.

19. A method as claimed in claim 1, comprising generating a plurality of consolidated sequences, wherein each of the plurality of consolidated sequences is generated using a different anchor sequence.

* * * * *

SEQUENCE LISTING

```
<160> NUMBER OF SEQ ID NOS: 142

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcttgtctag tca                                                          13

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```

```
ctgggttaca g                                                          11

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaaaaaaaaa cg                                                         12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acacacacac ac                                                         12

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaaaaaaaa cgaaaaaaaa aacgaaaaaa aaaacg                               36

<210> SEQ ID NO 6
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ctcgagaatt ctggatcctc cggcaggaat gaggcaagtc cagcctggcc gaggaggagg     60
agaagccatg gccatcataa ggacacaggc tacgcggctc atggcctggg tgt            113

<210> SEQ ID NO 7
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ctcgagaatt ctggatcctc aatctcaact aggtggaact aggcaaggaa caggtaggaa     60
gctgaattgg ctcgtgagat aacctaagag atatccagtg tctatgcagt acctattctt    120
gtgtacttat cttattcact ggaaccttct acaaccacat gcaat                    165

<210> SEQ ID NO 8
<211> LENGTH: 12
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 8
cctccggcag ga                                                              12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atgaggcaag tc                                                              12

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctggccgagg ag                                                              12

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
catggccatc at                                                              12

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aggaggagga ga                                                              12

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctggggttac ag                                                              12

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 14
ccaagcctcc cgagtagctg gggttacagg tg                                     32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agtagctggg gttacaggtg cctgccccac gg                                     32

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcccgagtag ctggggttac aggtgcctgc cc                                     32

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccgagtagct ggggttacag gtgcctgccc ca                                     32

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcccgagtag ctggggttac aggtgcctgc cc                                     32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctcccgagta gctggggtta caggtgcctg cc                                     32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
```
tagctggggt tacaggtgcc tgccccacgg cg                                  32

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtagctgggg ttacaggtgc ctgccccacg gc                                  32

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctggggttac aggtgcctgc cccacggcgc ct                                  32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtagctgggg ttacaggtgc ctgcccccg gc                                   32

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
caccccagcc tcccgagtag ctggggttac ag                                  32

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agctggggtt acaggtgcct gccccacggc gc                                  32

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tcccgagtag ctggggttac aggtgcctgc cc                                  32

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agctggggtt acaggtgcct gcccccggc gc                                      32

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ccagcctccc gagtagctgg ggttacaggt gc                                      32

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gtagctgggg ttacaggtgc ctgccccacg gc                                      32

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctcccgagta gctggggtta caggtgcctg cc                                      32

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
accccagcct cccgagtagc tggggttaca gg                                      32

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cctcccgagt agctggggtt acaggtgcct gc                                      32

-continued

```
<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcccgagtag ctggggttac aggtgcctgc cc                                    32

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
agcctcccaa ggtgctgggg ttacaggtgt ga                                    32

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tcccaaggtg ctggggttac aggtgtgagc c                                     31

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aggtgctggg gttacaggtg tgagccactg ca                                    32

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ccaaggtgct ggggttacag gtgtgagcca ct                                    32

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tcagcctccc aaggtgctgg ggttacaggt gt                                    32

<210> SEQ ID NO 39
<211> LENGTH: 32
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgctggggtt acaggtgtga gccactgcat tg                                    32

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcagcctccc aaggtgctgg ggttacaggt gt                                    32

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggtgctgggg ttacaggtgt gagccactgc at                                    32

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tcagcctccc aaggtgctgg ggttacaggt gt                                    32

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aggtgctggg gttacaggtg tgagccactg ca                                    32

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44 gtgctgggt tacaggtgtg agccactgca tt                                     32

<210> SEQ ID NO 45
<211> LENGTH: 32
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 45
gcctcccaag gtgctggggt tacaggtgtg ag                                     32

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aggtgctggg gttacaggtg tgagccactg ca                                     32

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ccaaggtgct ggggttacag gtgtgagcca ct                                     32

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tcagcctccc aaggtgctgg ggttacaggt gt                                     32

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agcgtcccaa ggtgctgggg ttacaggtgt ga                                     32

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gtgctggggt tacaggtgtg agccactgca tt                                     32

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 51
caaggtgctg gggttacagg tgtgagccac tg                        32

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ccaaggtgct ggggttacag gtgtgagcca ct                        32

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggtgctgggg ttacaggtgt gagccactgc at                        32

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cctcccaagg tgctggggtt acaggtgtga gc                        32

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ctcagcctcc caaggtgctg gggttacagg tg                        32

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agcctcccaa ggtgctgggg ttacaggtgt ga                        32

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 57
aggtgctggg gttacaggtg tgagccactg ca                                      32

<210> SEQ ID NO 58
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
caaggtgctg gggttacagg tgtgagccac tg                                      32

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 59
ctggggttac agccaaggtg gtgtgagc                                           28

<210> SEQ ID NO 60
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gcctcagcct cccaaggtgc tggggttaca ggtgtgagcc actgcattgg g                 51

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 61
ctggggttac agccgagtag gtgcctgc                                           28

<210> SEQ ID NO 62
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
caccccagcc tcccgagtag ctggggttac aggtgcctgc ccacggcgc ct                 52

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
```

-continued cgatcaaaag ggacaagcat caag                                          24

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
acgagttgcg tg                                                       12

<210> SEQ ID NO 65
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tcaagtccga agaccagatt cccgacgagt tgcgtgccca cttccgttat c            51

<210> SEQ ID NO 66
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
aagtccgaag accagattcc cgacgagttg cgtgcccact tccgttatcc t            51

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
caagtccgaa gaccagattc ccgacgagtt gcgtgcccac ttccgttatc c            51

<210> SEQ ID NO 68
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ccgaagacca gattcccgac gagttgcgtg cccacttccg ttatccggag g            51

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cagattcccg acgagttgcg tgcccacttc cgttatccgt actaccttt c             51

<210> SEQ ID NO 70
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gaagaccaga ttcccgacga gttgcgtgcc cacttccgtt atccggagga c            51

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
accgtcaagt ccgaagacca gattcccgac gagttgcgtg cccacttccg t            51

<210> SEQ ID NO 72
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gtccgaagac cagattcccg acgagttgcg tgcccacttc cgttatccgg a            51

<210> SEQ ID NO 73
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ccgaagacca gattcccgac gagttgcgtg cccacttccg ttatccgtag g            51

<210> SEQ ID NO 74
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aaccgtcaag tccgaagacc agattcccga cgagttgcgt gcccacttcc g            51

<210> SEQ ID NO 75
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
accagattcc cgacgagttg cgtgcccact tccgttatcc ggaggacctt t            51

<210> SEQ ID NO 76

```
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tccgaagacc agattcccga cgagttgcgt gcccacttcc gttatccgga g          51

<210> SEQ ID NO 77
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gaagaccaga ttcccgacga gttgcgtgcc cacttccgtt atccggagga c          51

<210> SEQ ID NO 78
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ccagattccc gacgagttgc gtgcccactt ccgttatccg gaggaccttt t          51

<210> SEQ ID NO 79
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
agtccgaaga ccagattccc gacgagttgc gtgcccactt ccgttatcct t          51

<210> SEQ ID NO 80
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ccgaagacca gattcccgac gagttgcgtg cccacttccg ttatccggag t          51

<210> SEQ ID NO 81
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cctttcccgg aaccgtcaag tccgaagacc agattcccga cgagttgcgt gcccacttcc    60
cgttatccgg aggaccttttt cgag                                          84

<210> SEQ ID NO 82
```

```
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
acgagttgcg cc                                                         12

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
acgagttgcg cc                                                         12

<210> SEQ ID NO 84
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
acgagttgtg cc                                                         12

<210> SEQ ID NO 85
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
acgagttgcg ga                                                         12

<210> SEQ ID NO 86
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
acgagttgcg gc                                                         12

<210> SEQ ID NO 87
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
acgagttgcg gc                                                         12

<210> SEQ ID NO 88
<211> LENGTH: 12
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 88
acgagttgcg gc                                                          12

<210> SEQ ID NO 89
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
acgagttgcg gc                                                          12

<210> SEQ ID NO 90
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
acgagttgcg tg                                                          12

<210> SEQ ID NO 91
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
acgagttgcg tg                                                          12

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
atgccagagg ctgctccccc cgtggcccct gcaccagcag                            40

<210> SEQ ID NO 93
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
atgccagagg ctgctccccs cgtggcccct gcaccagcag                            40

<210> SEQ ID NO 94
<211> LENGTH: 32
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 94
gagatgttcc gagagccttg gaactcaagg at                                    32

<210> SEQ ID NO 95
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gagatgttcc gagaggagat gtttggaact caaggat                               37

<210> SEQ ID NO 96
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotid

<400> SEQUENCE: 96
gagatgttcc gagaggacct tggaactcaa ggat                                  34

<210> SEQ ID NO 97
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotid

<400> SEQUENCE: 97
gagatgttcc gagaggagat gtcttggaac tcaagg                                36

<210> SEQ ID NO 98
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gagatgttcc gagaggagat gtcttggaac tcaagga                               37

<210> SEQ ID NO 99
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gagatgttcc gagaggagat gtcttggaac tcaaggat                              38

<210> SEQ ID NO 100
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 100
gagatgttcc gagaggagat gtcttggaac tcaaagat                                38

<210> SEQ ID NO 101
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgccagaggc tgctcccccc gtggcccctg caccagcag                               39

<210> SEQ ID NO 102
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
atgccagagg ctgctccccg cgtggcccct gccagcag                                38

<210> SEQ ID NO 103
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
atgccagagg cggctccccg cgtggcccct gcaccagcag                              40

<210> SEQ ID NO 104
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
atcagaggct gctccccgcg tggcccctgc accagcag                                38

<210> SEQ ID NO 105
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
atgccagagg ctgctccgcg tggcccctgc accagcag                                38

<210> SEQ ID NO 106
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106

```
atgccagagg ctgctccccc gtggcccctg caccagcag                            39
```

<210> SEQ ID NO 107
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107

```
atgcgaggct gctccccgcg tggcccctgc accagcag                             38
```

<210> SEQ ID NO 108
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108

```
atgccagagg ctgccccgcg tggcccctgc accagcag                             38
```

<210> SEQ ID NO 109
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109

```
atgccagagg gctcccccg tggcccctgc accagcag                              38
```

<210> SEQ ID NO 110
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110

```
atgccagagg ctgctccccg cgtgccctgc accagcag                             38
```

<210> SEQ ID NO 111
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111

```
atgccagagg ctgctccccg tggcccctgc accagcag                             38
```

<210> SEQ ID NO 112
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112

```
atgccagagg cttccccgcg tggcccctgc accagcag                             38
```

```
<210> SEQ ID NO 113
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
atgccagagg ctgctccgcg tggcccctgc accagcag                              38

<210> SEQ ID NO 114
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
atgccagagg ctgctccccg cgtggcctgc accagcag                              38

<210> SEQ ID NO 115
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atgccagagg ctgctccccg cgtggcccct gcaccca                               37

<210> SEQ ID NO 116
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
atgccagagg ctgctccccg cgtggcccct gcaccaag                              38

<210> SEQ ID NO 117
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
atgccagagg ctgctccccg cgtcccctgc accagcag                              38

<210> SEQ ID NO 118
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
atgccagagg ctgctccccc cgtggcccct gcaccaag                              38
```

```
<210> SEQ ID NO 119
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
aagggacaag catcaag                                                  17

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cgaagggaca agcatcaag                                                19

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cgatcaaaag acaagcatca ag                                            22

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cgatcaaaag ggaagcatca ag                                            22

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cgatcaaaag ggacgcatca ag                                            22

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
cgatcaaaag ggacacatca ag                                            22

<210> SEQ ID NO 125
<211> LENGTH: 22
```

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 125
cgatcaaagg ggacaagcca at                                              22

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126
cgatcaaaag ggacaagcaa ag                                              22

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 127
cgatcaacag ggacaagcca ag                                              22

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 128
cgctcaaaag ggacaagcca at                                              22

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 129
cgatcaagag ggacaagcca ag                                              22

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 130
cgatcaaaag ggacaagcca ag                                              22

<210> SEQ ID NO 131
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 131
cgatcaaaac aagcatcaag                                                   20

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
cgatcaaaaa gcatcaag                                                     18

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cgatcaaaag agcatcaag                                                    19

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
cgatcaaaag gggcatcaag                                                   20

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cgatcaaaag gcatcaag                                                     18

<210> SEQ ID NO 136
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cgatcaaaca tcaag                                                        15

<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
```

-continued

```
<400> SEQUENCE: 137
cgatcaaaag ggacaagca                                          19

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
cgatcaaaag ggacaatcaa g                                       21

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cgatcaaaag ggacaagcat caat                                    24

<210> SEQ ID NO 140
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
aagggacaag catcaag                                            17

<210> SEQ ID NO 141
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gggacaagca tcaag                                              15

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cgatcaggga caagcatcaa g                                       21
```